(12) United States Patent
Soliman et al.

(10) Patent No.: US 11,292,776 B2
(45) Date of Patent: Apr. 5, 2022

(54) SMALL MOLECULE INHIBITORS OF FUNGAL HYPHAE AND BIOFILM FORMATION

(71) Applicant: University of Sharjah, Sharjah (AE)

(72) Inventors: Sameh Soliman, Sharjah (AE); Ashraf Ibrahim, Los Angeles, CA (US); Rania Hamdy, Sharjah (AE); Ayman Noreddin, Sharjah (AE)

(73) Assignee: University of Sharjah, Sharjah (AE)

( * ) Notice: Subject to any disclaimer, the term of this patent is extended or adjusted under 35 U.S.C. 154(b) by 0 days.

(21) Appl. No.: 16/711,839

(22) Filed: Dec. 12, 2019

(65) Prior Publication Data

US 2021/0179571 A1   Jun. 17, 2021

(51) Int. Cl.
*C07D 277/36* (2006.01)
*A61P 31/10* (2006.01)
*A61K 45/06* (2006.01)

(52) U.S. Cl.
CPC ............ *C07D 277/36* (2013.01); *A61P 31/10* (2018.01); *A61K 45/06* (2013.01)

(58) Field of Classification Search
CPC .................................................. C07D 277/36
See application file for complete search history.

(56) References Cited

U.S. PATENT DOCUMENTS 6,251,928 B1 * 6/2001 Panetta ................ C07D 277/20
514/369

OTHER PUBLICATIONS

Arora, et al. Document No. 151:358735 retrieved from STN; 2009.*
Bursavich, et al. Document No. 146:414263, retreived from STN; 2007.*
Geldenhuys, et al. Document No. 165:552715, retrieved from STN; 2016.*
Mckee, et al. Document No. 140:315042, retrieved from STN; 2004.*
Olsen, et al. Document No. 138:287978, retrieved from STN; (2003).*
Strittmatter, et al. Document No. 154:379103, retrieved from STN; (2011).*
Wang, et al. Document No. 156:656539, retrieved from STN; (2012).*

* cited by examiner

*Primary Examiner* — Shawquia Jackson
(74) *Attorney, Agent, or Firm* — Hayes Soloway P.C.

(57) ABSTRACT

Novel compounds having inhibitory activity on the formation of fungal hyphae and biofilms, and therapeutic formulations and methods based on the novel inhibitors.

20 Claims, 12 Drawing Sheets
Specification includes a Sequence Listing.

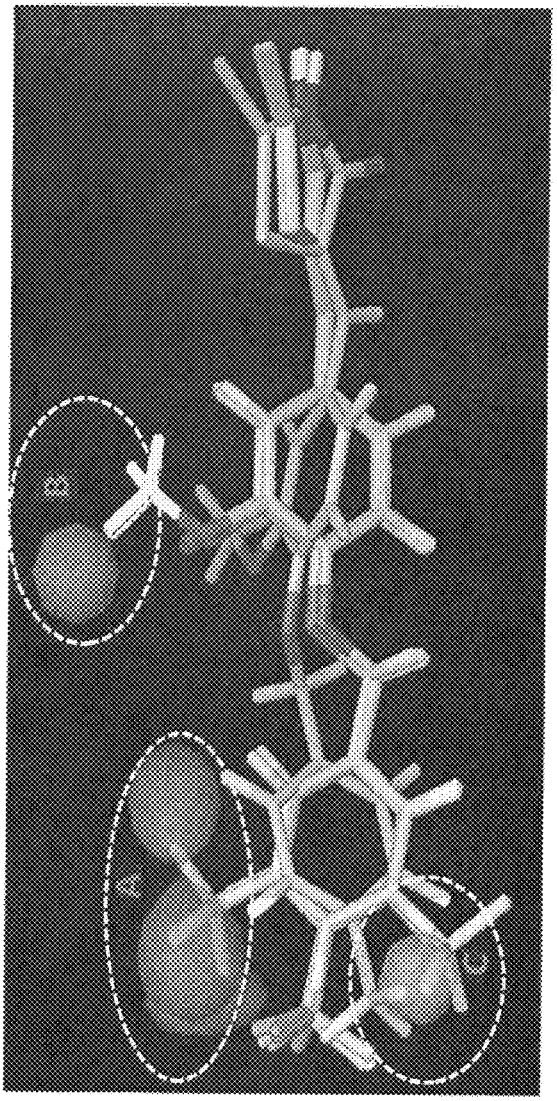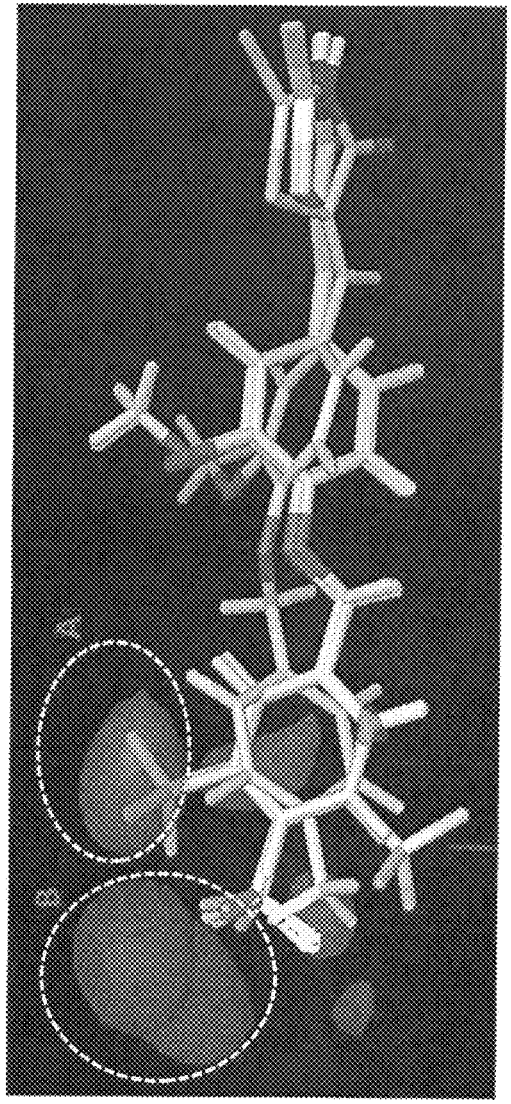
FIG. 7

| Models | SR1 | SR2 | SR3 | SR4 | SR5 | SR6 | SR7 | SR8 |
|---|---|---|---|---|---|---|---|---|
| Human Intestinal Absorption | HIA+ | HIA+ | HIA+ | HIA+ | HIA+ | HIA+ | HIA+ | HIA+ |
| CaCO-2 Permeability | CaCO2+ | CaCO2+ | CaCO2+ | CaCO2+ | CaCO2+ | CaCO2+ | CaCO2+ | CaCO2+ |
| P-glycoprotein Substrate | Non-substrate | Non-substrate | Non-substrate | Non-substrate | Non-substrate | Non-substrate | Non-substrate | Non-substrate |
| Renal Organic Cation Transporter | Non-inhibitor | Non-inhibitor | Non-inhibitor | Non-inhibitor | Non-inhibitor | Non-inhibitor | Non-inhibitor | Non-inhibitor |
| CYP450 2D6 Inhibitor | Non-inhibitor | Non-inhibitor | Non-inhibitor | Non-inhibitor | Non-inhibitor | Non-inhibitor | Non-inhibitor | Non-inhibitor |
| Human Ether-a-go-go-Related Gene Inhibition I | Weak Inhibitor | Weak Inhibitor | Weak Inhibitor | Weak Inhibitor | Weak Inhibitor | Weak Inhibitor | Weak Inhibitor | Weak Inhibitor |
| Human Ether-go-go-Related Gene Inhibition II | Non-inhibitor | Non inhibitor | Non inhibitor | Non inhibitor | Non-inhibitor | Non-inhibitor | Non-inhibitor | Non-inhibitor |
| AMES Toxicity | AMES toxic | Non AMES toxic | Non AMES toxic | Non AMES toxic | Non AMES toxic | Non AMES toxic | Non AMES toxic | Non AMES toxic |
| Carcinogens | Non-carcinogenic | Non-carcinogenic | Non-carcinogenic | Non-carcinogenic | Non-carcinogenic | Non-carcinogenic | Non-carcinogenic | Non-carcinogenic |
| Biodegradation | Not ready | Not ready | Not ready | Not ready | Not ready | Not ready | Not ready | Not ready |
| Acute Oral Toxicity | III | III | III | III | III | III | III | III |
| Carcinogenicity (Three class) | Non-Required | Non-Required | Non-Required | Non-Required | Non-Required | Non-Required | Non-Required | Non-Required |
| Rat Acute Toxicity LD50, mol/kg | 2.68 | 2.68 | 2.70 | 2.61 | 2.68 | 2.68 | 2.70 | 2.61 |
| Aqueous Solubility | -4.88 | -4.88 | -4.31 | -5.11 | -4.88 | -4.88 | -4.31 | -5.11 |
| TPSA | 79.65 | 70.42 | 70.42 | 79.65 | 70.42 | 70.42 | 79.65 | 70.42 |

FIG. 11

| Species | Reference body weight (kg) | Working weight range (kg) | Body surface area (m²) | To convert dose in mg/kg to dose in mg/m², multiply by $K_m$ | To convert animal dose in mg/kg to HED in mg/kg, either | |
|---|---|---|---|---|---|---|
| | | | | | divide animal dose by | Multiply animal dose by |
| Human | 60 | | 1.62 | 37 | | |
| Mouse | 0.02 | 0.011-0.034 | 0.007 | 3 | 12.3 | 0.081 |
| Hamster | 0.08 | 0.047-0.157 | 0.016 | 5 | 7.4 | 0.135 |
| Rat | 0.15 | 0.08-0.27 | 0.025 | 6 | 6.2 | 0.162 |
| Ferret | 0.30 | 0.16-0.54 | 0.043 | 7 | 5.3 | 0.189 |
| Guinea pig | 0.40 | 0.208-0.700 | 0.05 | 8 | 4.6 | 0.216 |
| Rabbit | 1.8 | 0.9-3.0 | 0.15 | 12 | 3.1 | 0.324 |
| Dog | 10 | 5-17 | 0.50 | 20 | 1.8 | 0.541 |
| Monkeys (rhesus) | 3 | 1.4-4.9 | 0.25 | 12 | 3.1 | 0.324 |
| Marmoset | 0.35 | 0.14-0.72 | 0.06 | 6 | 6.2 | 0.162 |
| Squirrel monkey | 0.60 | 0.29-0.97 | 0.09 | 7 | 5.3 | 0.189 |
| Baboon | 12 | 7-23 | 0.60 | 20 | 1.8 | 0.541 |
| Micro pig | 20 | 10-33 | 0.74 | 27 | 1.4 | 0.730 |
| Mini pig | 40 | 25-64 | 1.14 | 35 | 1.1 | 0.946 |

FIG. 12

SEQUENCE LISTING

<160> NUMBER OF SEQ ID NOS: 14

<210> SEQ ID NO 1
<211> LENGTH: 26
<212> TYPE: DNA
<213> ORGANISM: Artificial Sequence
<220> FEATURE:
<223> OTHER INFORMATION: Variant Nucleotide Sequence

<400> SEQUENCE: 1
caacttgggt tattgaaaca aaaaca                                                26

<210> SEQ ID NO 2
<211> LENGTH: 24
<212> TYPE: DNA
<213> ORGANISM: Artificial Sequence
<220> FEATURE:
<223> OTHER INFORMATION: Variant Nucleotide Sequence

<400> SEQUENCE: 2
agaaacagaa acccaagaac aacc                                                  24

<210> SEQ ID NO 3
<211> LENGTH: 20
<212> TYPE: DNA
<213> ORGANISM: Artificial Sequence
<220> FEATURE:
<223> OTHER INFORMATION: Variant Nucleotide Sequence

<400> SEQUENCE: 3
tgtgatggcg gttcttgttc                                                       20

<210> SEQ ID NO 4
<211> LENGTH: 25
<212> TYPE: DNA
<213> ORGANISM: Artificial Sequence
<220> FEATURE:
<223> OTHER INFORMATION: Variant Nucleotide Sequence

<400> SEQUENCE: 4
ggtagtgacg gtgatgatag tgaca                                                 25

<210> SEQ ID NO 5
<211> LENGTH: 20
<212> TYPE: DNA
<213> ORGANISM: Artificial Sequence
<220> FEATURE:
<223> OTHER INFORMATION: Variant Nucleotide Sequence

<400> SEQUENCE: 5
ccaagtacct ccaccagcat                                                       20

<210> SEQ ID NO 6
<211> LENGTH: 20
<212> TYPE: DNA
<213> ORGANISM: Artificial Sequence
<220> FEATURE:
<223> OTHER INFORMATION: Variant Nucleotide Sequence

<400> SEQUENCE: 6
gggagttggc cagtaaatca                                                       20

<210> SEQ ID NO 7
<211> LENGTH: 20
<212> TYPE: DNA
<213> ORGANISM: Artificial Sequence
<220> FEATURE:
<223> OTHER INFORMATION: Variant Nucleotide Sequence

<400> SEQUENCE: 7
cttggagttg gcccatagaa                                                       20

<210> SEQ ID NO 8

```
<211> LENGTH: 20
<212> TYPE: DNA
<213> ORGANISM: Artificial Sequence
<220> FEATURE:
<223> OTHER INFORMATION: Artificial Nucleotide Sequence

<400> SEQUENCE: 8
tggtgccaca atctgttgtt                                               20

<210> SEQ ID NO 9
<211> LENGTH: 20
<212> TYPE: DNA
<213> ORGANISM: Artificial Sequence
<220> FEATURE:
<223> OTHER INFORMATION: Variant Nucleotide Sequence

<400> SEQUENCE: 9
gctcctgctc ctgaaatgac                                               20

<210> SEQ ID NO 10
<211> LENGTH: 20
<212> TYPE: DNA
<213> ORGANISM: Artificial Sequence
<220> FEATURE:
<223> OTHER INFORMATION: Variant Nucleotide Sequence

<400> SEQUENCE: 10
ctggagcaat tggtgaggtt                                               20

<210> SEQ ID NO 11
<211> LENGTH: 20
<212> TYPE: DNA
<213> ORGANISM: Artificial Sequence
<220> FEATURE:
<223> OTHER INFORMATION: Variant Nucleotide Sequence

<400> SEQUENCE: 11
accaccacta ccaccaccac                                               20

<210> SEQ ID NO 12
<211> LENGTH: 20
<212> TYPE: DNA
<213> ORGANISM: Artificial Sequence
<220> FEATURE:
<223> OTHER INFORMATION: Variant Nucleotide Sequence

<400> SEQUENCE: 12
tatccccatt tccaagtcca                                               20

<210> SEQ ID NO 13
<211> LENGTH: 20
<212> TYPE: DNA
<213> ORGANISM: Artificial Sequence
<220> FEATURE:
<223> OTHER INFORMATION: Variant Nucleotide Sequence

<400> SEQUENCE: 13
cacgacggag tttcacaaga                                               20

<210> SEQ ID NO 14
<211> LENGTH: 20
<212> TYPE: DNA
<213> ORGANISM: Artificial Sequence
```

-continued

```
<220> FEATURE:
<223> OTHER INFORMATION: Variant Nucleotide Sequence

<400> SEQUENCE: 14
cgatggaagt ttgaggcaat                                              20
```

SMALL MOLECULE INHIBITORS OF FUNGAL HYPHAE AND BIOFILM FORMATION

REFERENCE TO AN ELECTRONIC SEQUENCE LISTING

The contents of the electronic sequence listing (Tamimi_1935_Sequence_Listing).txt; Size: 3,050 bytes; and Date of Creation: May 6, 2020) is herein incorporated by reference in its entirety.

TECHNICAL FIELD

The present invention relates to novel compounds having inhibitory activity on the formation of fungal hyphae and biofilms, and therapeutic formulations and methods based on the novel inhibitors.

BACKGROUND

*C. albicans* mostly causes superficial easily treated infections. However, it can hematogenously disseminate to become life-threatening particular with immunocompromised patients or those receiving broad spectrum antibiotic treatments. In fact, *C. albicans* is one of the most common causes of healthcare-associated bloodstream infections. *C. albicans* can switch between two major forms, yeast and hyphal forms. The switch from yeast to hyphae is recognized as one of the most virulent traits of *C. albicans*, since it is associated with the ability of the fungus to invade host tissues and form drug-resistance biofilms.

Biofilms are architecturally complex structures consisting of basal yeast cells and poly-layers of hyphae encapsulated in extracellular matrix. Thus, biofilms are inherently resistant to most antifungal treatments, provide haven for *C. albicans* from host defenses and constitute a reservoir for recurrent infection. Consequently, biofilm structures are often the cause of failed antifungal treatment, and indeed are associated with greater mortality of patients with candidemia. The contribution of biofilm formation to *C. albicans* pathogenicity and drug resistance emphasizes the need for new anti-hyphae agents that can inhibit *Candida* biofilm formation and hence prevents recalcitrant infection.

Quorum sensing (QS) molecules accumulated in the extracellular *Candida* environment can affect the morphological characteristics of the pathogen, forcing the formation of hyphae and thereby favoring biofilm formation and resistance to antimicrobial agents. The best characterized QS molecule involved in *C. albicans* biofilm formation is farnesol, which suppresses filament formation and reduces biofilm size. Taken in consideration the specific behavior of QS molecules, we have been able to design new compounds with farnesol-like function, despite of structural differences.

It has been reported that thiazolidinedione derivatives (FIG. 1) exert significant inhibitory activities against *C. albicans* hyphal growth. Similarly, rhodanine derivatives showed inhibitory effects on *C. albicans* biofilm, bacterial biofilm and numerous fungal targets including mannosyl transferase 1 (PMT1). Furthermore, aromatic compounds such as 1,2-benzisothiazolinone and pyridine-rhodanine derivatives (FIG. 1) showed potent anti-*Candida* activities.

SUMMARY OF THE EMBODIMENTS

In accordance with a first aspect of the present disclosure, there is provided a compound of Formula (SR):

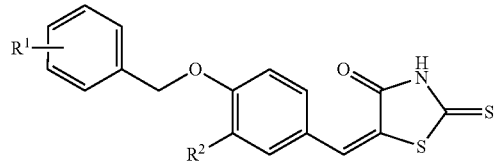

Formula (SR)

wherein: $R^1$ is selected from a halogen atom, CN, $NO_2$, $R^3$, $OR^3$, $SR^3$, $N(R^3)_2$, $C(O)R^3$, $C(O)OR^3$, $NR^3C(O)R^3$, $C(O)NR^3$, $SO_2R^3$, $NR^3SO_2R^3$, and $SO_2N(R^3)_2$; $R^3$ is a $C_1$-$C_5$ alkyl group optionally substituted with one or more halogen atoms; $R^2$ is a halogen atom, CN, $NO_2$, $R^4$, $OR^4$, $SR^4$, $N(R^4)_2$, $C(O)R^4$, $C(O)OR^4$, $NR^4C(O)R^4$, $C(O)NR^4$, $SO_2R^4$, $NR^4SO_2R^4$, and $SO_2N(R^4)_2$; $R^4$ is a $C_1$-$C_5$ alkyl group optionally substituted with one or more halogen atoms. In an embodiment, wherein $R^3$ is selected from $CH_3$, $CH_2X$, $CHX_2$, and $CX_3$, wherein X is a halogen atom. In another embodiment, $R^3$ is selected from $CH_3$ and $CF_3$. In a further embodiment, $R^3$ is selected from $CH_3$ and $CF_3$. In an additional embodiment, $R^4$ is selected from $CH_3$, $CH_2X$, $CHX_2$, and $CX_3$, wherein X is a halogen atom. In another embodiment, $R^1$ is $CF_3$ and $R^2$ is $OCH_3$. In a non-limiting embodiment, the compound is of Formula (SR1) or Formula (SR2):

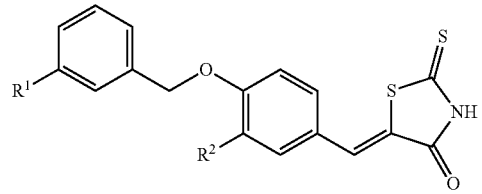

Formula (SR1)

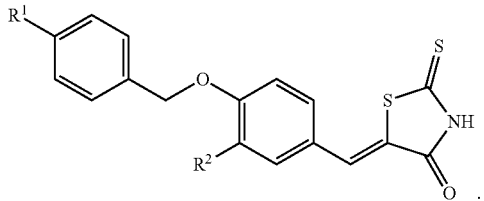

Formula (SR2)

In accordance with a second aspect of the present disclosure, there is provided a therapeutic composition for treating, suppressing, or reducing the severity of hyphal formation, the composition comprising a compound of Formula (SR).

In accordance with a third aspect of the present disclosure, there is provided a method of treating, suppressing, or reducing the severity of hyphal formation in a subject with a fungal infection, the method comprising administering to the subject a therapeutic amount of a compound of Formula (SR):

Formula (SR)

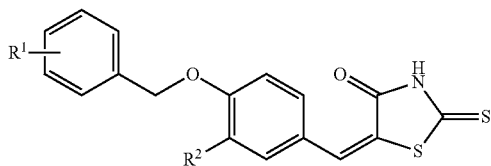

wherein: $R^1$ is selected from a halogen atom, CN, $NO_2$, $R^3$, $OR^3$, $SR^3$, $N(R^3)_2$, $C(O)R^3$, $C(O)OR^3$, $NR^3C(O)R^3$, $C(O)NR^3$, $SO_2R^3$, $NR^3SO_2R^3$, and $SO_2N(R^3)_2$; $R^3$ is a $C_1$-$C_5$ alkyl group optionally substituted with one or more halogen atoms; $R^2$ is a halogen atom, CN, $NO_2$, $R^4$, $OR^4$, $SR^4$, $N(R^4)_2$, $C(O)R^4$, $C(O)OR^4$, $NR^4C(O)R^4$, $C(O)NR^4$, $SO_2R^4$, $NR^4SO_2R^4$, and $SO_2N(R^4)_2$; $R^4$ is a $C_1$-$C_5$ alkyl group optionally substituted with one or more halogen atoms. In an embodiment, wherein $R^3$ is selected from $CH_3$, $CH_2X$, $CHX_2$, and $CX_3$, wherein X is a halogen atom. In another embodiment, $R^3$ is selected from $CH_3$ and $CF_3$. In a further embodiment, $R^3$ is selected from $CH_3$ and $CF_3$. In an additional embodiment, $R^4$ is selected from $CH_3$, $CH_2X$, $CHX_2$, and $CX_3$, wherein X is a halogen atom. In another embodiment, $R^1$ is $CF_3$ and $R^2$ is $OCH_3$. In a non-limiting embodiment, the compound is of Formula (SR1) or Formula (SR2):

Formula (SR1)

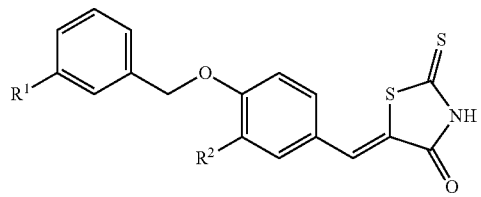

Formula (SR2)

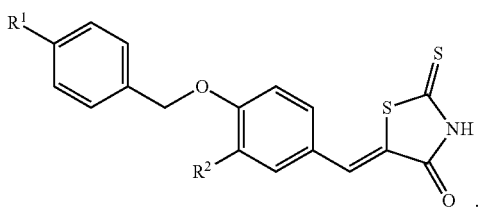

In an embodiment, the fungal infection is a yeast of the genus *Candida*, for example *Candida albicans*.

In accordance with a third aspect of the present disclosure, there is provided a combination of drugs for the treatment of a fungal infection, the combination comprising a compound a compound of Formula (SR) and an antifungal agent. The antifungal agent may be selected from the group consisting of azole antifungals, echinocandins, polyenes, griseofulvin, terbinafine, flucytosine, terbinafine, and combinations thereof.

In accordance with a fourth aspect of the present disclosure, there is provided an improved method of treating, suppressing, or reducing the severity of a fungal infection in a subject, the method comprising: administering a first amount of an antifungal agent, the improvement comprising administering to the subject a second amount of a compound of Formula (SR). In an embodiment, the fungal infection is of the genus *Candida*, such as *Candida aibicans*.

BRIEF DESCRIPTION OF THE FIGURES

The invention can be better understood with reference to the following figures and description. The components in the figures are not necessarily to scale and are not intended to accurately represent molecules, cells, cell organelles, tissues, or their interactions, emphasis instead being placed upon illustrating the principles of the invention.

FIG. 7 is a 3DQSAR contour map of synthesized compounds, the fields were shown as surfaces, and the compounds were aligned together. (A) Sterically-favored area was shown in green-colored contours and sterically-unfavored area was shown in yellow-colored contours. (B) Positively-potential favored areas are shown in blue-colored contours and negatively potential favored areas are shown in red-colored contours.

FIG. 11 reports predicted ADMET properties of example synthesized compounds.

FIG. 12 is a table reporting human equivalent dose (HED) dosage factors based on body surface area of other species according to data obtained from Food and Drug Administration draft guidelines.

DETAILED DESCRIPTION OF SPECIFIC EMBODIMENTS

Figure 1:
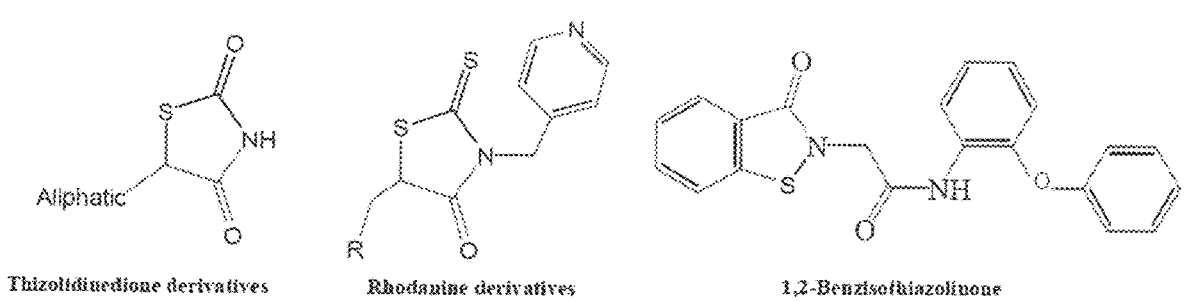
FIG. 1 illustrates the structures of thiazolidinedione, pyridine-rhodanine and 1,2-benzisothiazolinone derivatives.

In a first aspect of the present application, provided herein are 5-[3-substituted-4-(4-substituedbenzyloxy)-benzylidene]-2-thioxo-thiazolidin-4-one (SR) compounds having a hybrid molecular structure of Formula (SR):

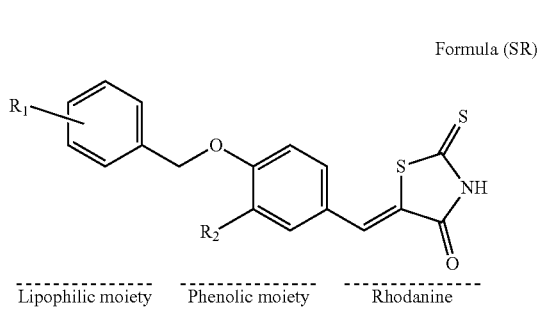

Formula (SR)

Lipophilic moiety    Phenolic moiety    Rhodanine

The hybrid structure includes a rhodanine analogue moiety coupled with a side chain made of two fused aromatic structures. In representative embodiments, Moiety $R^1$ is selected from a halogen atom, CN, $NO_2$, $R^3$, $OR^3$, $SR^3$, $N(R^3)_2$, $C(O)R^3$, $C(O)OR^3$, $NR^3C(O)R^3$, $C(O)NR^3$, $SO_2R^3$, $NR^3SO_2R^3$, and $SO_2N(R^3)_2$, where $R^3$ is a $C_1$-$C_5$ alkyl group optionally substituted with one or more halogen atoms. In some embodiments, $R^3$ is $CH_3$, $CH_2X$, $CHX_2$, or $CX_3$, where X is a halogen atom. In a non-limiting embodiment, $R^1$ is an electron-withdrawing group, for example $CF_3$, $NO_2$, or halogen, at position 3 on the benzene ring. In another non-limiting embodiment, $R^1$ is an electron-donating group, for example alkyl, amino, or alkoxy, at position 4 on the benzene ring. Moiety $R^2$ is a halogen atom, CN, $NO_2$, $R^4$, $OR^4$, $SR^4$, $N(R^4)_2$, $C(O)R^4$, $C(O)OR^4$, $NR^4C(O)$ $R^4$, $C(O)NR^4$, $SO_2R^4$, $NR^4SO_2R^4$, or $SO_2N(R^4)_2$, where $R^4$ is a $C_1$-$C_5$ alkyl group optionally substituted with one or more halogen atoms. In representative embodiments, moiety $R^4$ is $CH_3$, $CH_2X$, $CHX_2$, or $CX_3$, where X is a halogen atom.

These newly designed 5-[3-substituted-4-(4-substitued-benzyloxy)-benzylidene]-2-thioxo-thiazolidin-4-one derivatives, hereinafter named "SR compounds", have shown very specific and effective inhibition activity against *C. albicans* hyphae formation. SR compounds caused hyphae inhibition activity at concentrations 10- to 40-fold lower than the concentration required to inhibit *Candida* yeast and bacterial growths. Without being bound to any particular theory, it appears that the anti-hyphal inhibitory activity of SR compounds took place via activation of the hyphae transcription repressor, TUP1. Correlation and 3D quantitative structure-activity relationship (QSAR) modelling studies confirmed that anti-*C. albicans* activity on the part of SR compounds occurred via inhibition of hyphae formation. The newly designed SR compounds showed 10-40% hemolytic activity on human erythrocytes when compared to 100% haemolysis by 0.1% triton as positive control. Furthermore, theoretical prediction of absorption, distribution, metabolism, excretion, and toxicity (ADMET) of SR compounds confirmed their safety, efficient metabolism and possible oral bioavailability. With their minimal toxicity, the newly-designed SR compounds are candidates for the effective use of adjunctive therapy with currently used antifungal agents to ameliorate infections due to *C. albicans* and other TUP1-dependent dimorphic fungal infections.

Chemistry of the SR Compounds

In another aspect, an exemplary synthetic route of 5-[3-substitued-4-(4-substituedbenzyloxy)-benzylidene]-2-thioxo-thiazolidin-4-one (SR) compounds of Formula (SR) is described in Scheme 1:

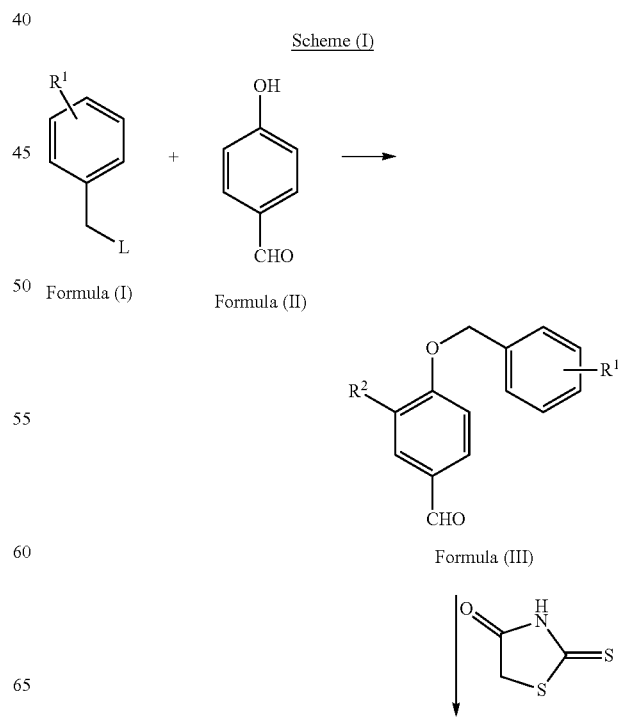

Scheme (I)

Formula (I)    Formula (II)

Formula (III)

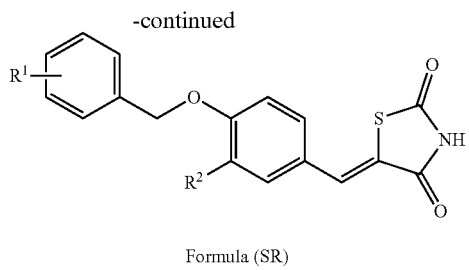

Formula (SR)

Figure 2:
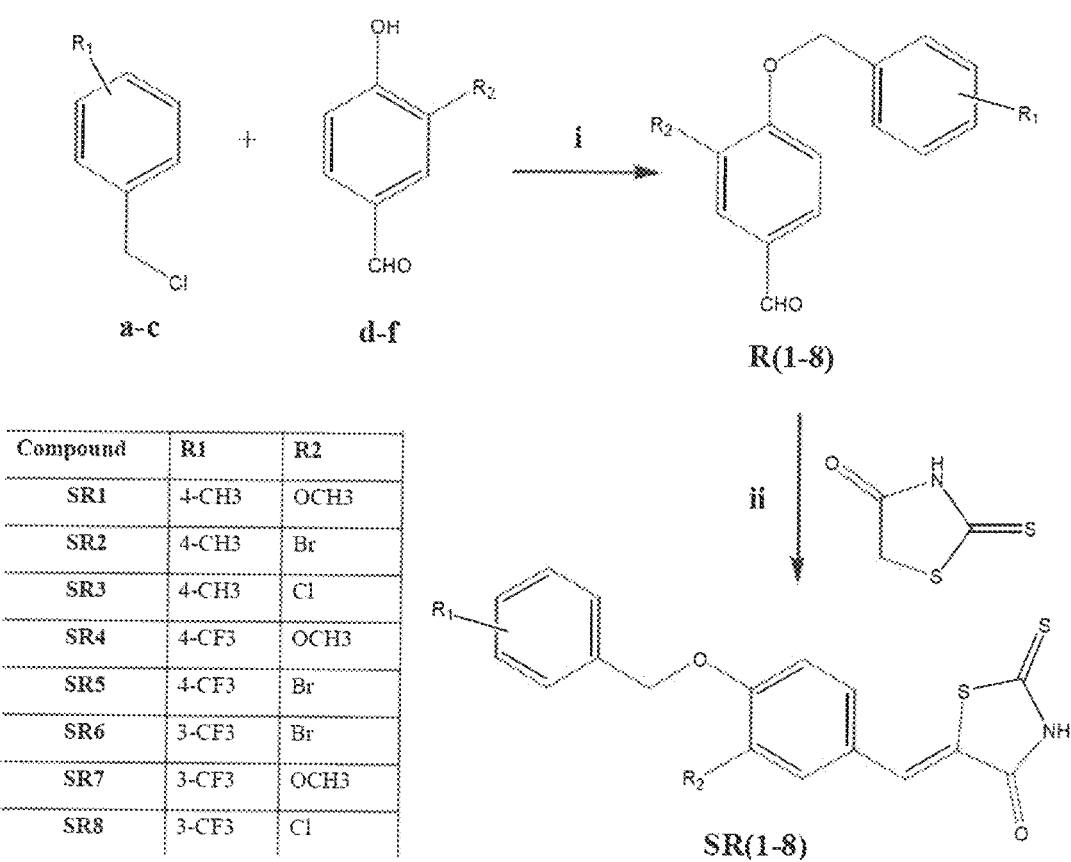
FIG. 2 illustrates the synthesis scheme of example 5-[3-Substitued-4-(4-substituedbenzyloxy)-benzylidene]-2-thioxo-thiazolidin-4-one derivatives. Reagents and conditions: i. $K_2CO_3$, KI, acetonitrile, overnight stirring under nitrogen; ii. β-alanine, glacial acetic acid, 100° C., 3 h; $R_1$. $CH_3$, $3CF_3$, $4CF_3$; $R_2$. Cl, Br, $OCH_3$.

A substituted benzyl precursor of Formula (I), where L is a leaving group such as halogen or tosylate, is reacted with the substituted 4-hydroxybenzaldehyde of Formula (II), to obtain the 3-substituted-4-(4-substituedbenzyloxy) benzaldehyde of Formula (II) which is reacted with rhodanine via Knoevenagel condensation reaction to yield a final product of Formula (SR). This process is exemplified in the synthesis outlined in FIG. 2, where the intermediate 3-substituted-4-(4-substituedbenzyloxy) benzaldehyde (R1-8) was synthesized by coupling substituted-benzyl chloride (a-c) with 3-substituted-4-hydroxybenzaldehyde in the presence of $K_2CO_3$ and KI in acetonitrile. The obtained compounds (R1-8) were then reacted with rhodanine in the presence of β-alanine and glacial acetic acid via Knoevenagel condensation reactions in order to provides 5-[3-substitued-4-(4-substituedbenzyloxy)-benzylidene]-2-thioxo-thiazolidin-4-one derivatives, SR1-8 (FIG. 2).

Formulations of Sr Compounds

In another aspect, the present application provides therapeutic methods to treat, suppress, inhibit, or reduce the severity of hyphal formation in a subject by administering a therapeutically effective amount of an SR compound, either alone or formulated together with one or more pharmaceutically acceptable carrier(s), diluent(s), or excipient(s). The carrier(s), diluent(s) or excipient(s) must be acceptable in the sense of being compatible with the other ingredients of the formulation, capable of pharmaceutical formulation, and not deleterious to the recipient thereof.

Unless otherwise specified, the terms "composition including SR compound" and "formulation of SR compound" as used herein are intended to cover compositions and formulations including one or more SR compounds as defined herein.

In instances where a derivative of an SR compound is pharmaceutically acceptable and easily cleavable under physiological conditions, one or more derivative may be administered to the patient as a pro-drug of the SR compound itself. The term "pharmaceutically acceptable SR compound derivative", in this respect, refers to the pharmaceutically acceptable and easily cleavable groups of the SR compound derivative, including hemiacetals, acetals, thioketals, silyl ethers, and nucleophilic addition products. These pro-drugs can be prepared in situ in the administration vehicle or in the dosage form manufacturing process, or by separately reacting the SR compound with a suitable reactant, and isolating the derivative thus formed during subsequent purification. Other derivatives that may serve as pro-drugs include pharmaceutically acceptable salts and hydrates. Therapeutically effective tautomers and isomers of an SR compound are also contemplated.

Unless otherwise specified, the terms "composition of an SR compound", "composition including an SR compound", and "formulation of and SR compound" as used herein are intended to cover compositions and formulations including the SR compound itself and/or its pro-drugs such as: hemiacetals and acetals, pharmaceutically acceptable tautomers and isomers, and pharmaceutically acceptable salts thereof.

Compositions featuring SR compounds may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

The formulations may conveniently be presented in unit dosage form and may be prepared by any methods well known in the art of pharmacy. The amount of SR compound which can be combined with a carrier material to produce a single dosage form will vary depending upon the subject being treated, the particular mode of administration. The amount of an active ingredient which can be combined with a carrier material to produce a single dosage form will usually be that amount of the compound which produces a therapeutic effect. Usually, out of one hundred percent, this amount will range from about 1 wt % to about 99 wt % of active ingredient, preferably from about 5 wt % to about 70 wt %, most preferably from about 10 wt % to about 30 wt %.

In certain embodiments, a formulation of SR compound includes an excipient selected from the group consisting of cyclodextrins, liposomes, micelle forming agents, e.g., bile acids, and polymeric carriers, e.g., polyesters and polyanhydrides; and an active ingredient that may be SR compound and/or one of its pharmaceutically acceptable derivatives. In certain embodiments, an aforementioned formulation renders orally bioavailable an SR compound or its derivative.

Methods of preparing these formulations or compositions include the step of bringing into association SR compound with the carrier and, optionally, one or more accessory ingredients. Usually, the formulations are prepared by uniformly and intimately bringing into association a compound of the present invention with liquid carriers, or finely divided solid carriers, or both, and then, if necessary, shaping the product.

Liquid dosage forms for oral administration of SR compound include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents. Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A formulation of SR compound may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol, glycerol monostearate, and non-ionic surfactants; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also include buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

The tablets, and other solid dosage forms of the formulation of SR compound, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Formulations of the pharmaceutical compositions of SR compound for rectal or vaginal administration may be presented as a suppository, which may be prepared by mixing SR compound with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Dosage forms for the topical or transdermal administration of SR compound include powders, sprays, ointments, pastes, creams, lotions, gels, solutions, patches and inhalants. The extract may be mixed under sterile conditions with a pharmaceutically-acceptable carrier, and with any preservatives, buffers, or propellants which may be required. The ointments, pastes, creams and gels may contain, in addition to an extract, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an extract, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of SR compound to the body. Such dosage forms can be made by dissolving or dispersing an extract in the proper medium. Absorption enhancers can also be used to increase the flux of the extract or dispersing the extract in a polymer matrix or gel.

Pharmaceutical compositions suitable for parenteral administration include one or more components of an SR compound in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Regardless of the route of administration selected, SR compound may be formulated into pharmaceutically-acceptable dosage forms by conventional methods known to those of skill in the art. SR compound may be formulated for administration in any convenient way for use in human or veterinary medicine, by analogy with other pharmaceuticals.

In certain embodiments, the above-described pharmaceutical compositions include SR compound, a traditional antifungal agent, and optionally a pharmaceutically acceptable carrier. Alternatively, the term "antifungal agent" is understood to include, for example, azole antifungals such as itraconazole, posaconazole, fluconazole, ketoconazole, clotrimazole, isavuconazonium, itraconazole, mitroconazole, itraconazole; echinocandins such as caspofungin, anidulafungin, micafungin; polyenes such as nystatin, amphotericins; and other antifungals such as griseofulvin, terbinafine, flucytosine, and terbinafine.

Methods of Treatment

In a further aspect, the above SR compound compositions may be used in novel therapeutic methods of inhibiting the formation of hyphae in a patient suffering from a fungal infection. The methods include administering to a subject an effective amount of a pharmaceutical SR compound composition. In representative embodiments, the subject suffers from an infection from a yeast of the genus *Candida*, for example *Candida albicans*. In specific embodiments, the SR composition may be administered in conjunction with traditional antifungal agents as an adjuvant for preventing formation of hyphae.

As anticipated above, the SR compound formulation may be administered by any appropriate route, for example orally, parenterally, topically, or rectally. It will be appreciated that the preferred route may vary with, for example, the condition of the recipient of the SR compound formulation and the infection to be treated. In certain embodiments, the compound may be especially suitable for the preparation of pharmaceuticals for intravenous administration, such as intravenous injection or infusion, provided that it does not contain components with serum-precipitating and/or haemagglutinating properties which disturb such an application. The SR compound may therefore be provided in the form of ampoule preparations which are directed to intravenous administration. In still other embodiments, the method comprises systemic administration of a subject composition to a subject.

Also provided are methods of treating fungal infections, for example *C. albicans*, which include administering an SR compound in conjunction with a traditional antifungal to a subject. Conjunctive therapy includes sequential, simultaneous and separate, or co-administration of the SR compound and the traditional antifungal in a way that the therapeutic effect of the antifungal is not entirely disappeared when the SR compound is administered. In certain embodiments, the SR compound and the antifungal may be compounded together in the same unitary pharmaceutical composition including both entities. Alternatively, the combination of the SR compound and the antifungal may be administered separately in separate pharmaceutical compositions, each including one of the SR compound and one of the antifungal in a sequential manner wherein, for example, the SR compound or the antifungal is administered first and the other second.

Exemplary doses of SR compound fall in the range from about 0.001, 0.01, 0.1, 0.5, 1, 10, 15, 20, 25, 50, 100, 200, 300, 400, 500, 600, or 750 to about 1000 mg/day per kg body weight of the subject. In certain embodiments, the dose of SR compound will typically be in the range of about 100 mg/day to about 1000 mg/day per kg body weight of the subject, specifically in the range of about 200 mg/day to about 750 mg/day per kg, and more specifically in the range of about 250 mg/day to about 500 mg/day per kg. In an embodiment, the dose is in the range of about 50 mg/day to about 250 mg/day per kg. In a further embodiment, the dose in the range of about 100 mg/day to about 200 mg/day per kg. In an embodiment, the dose is in the range of about 15 mg/day to 60 mg/day per kg. In a further embodiment, the dose is in the range of about 20 mg/day to 50 mg/day per kg. In an additional embodiment, the dose is in the range of about 25 mg/day to 45 mg/day per kg.

The combined use of SR compound and traditional antifungals may reduce the required dosage for any individual component because the onset and duration of effect of the different components may be complementary. In such combination therapies, the different active agents may be delivered together or separately, and simultaneously or at different times within the day.

The data obtained from cell culture assays and animal studies may be used in formulating a range of dosage for use in humans. For example, effective dosages achieved in one animal species may be extrapolated for use in another animal, including humans, as illustrated in the conversion table of FIG. 12 where human equivalent dose (HED) dosage factors based on body surface area of other species are reported. [69]. The dosage of any supplement, or alternatively of any components therein, lies preferably within a range of circulating concentrations that include the $ED_{50}$ with little or no toxicity. The dosage may vary within this range depending upon the dosage form employed and the route of administration utilized. For SR compounds or combinations of SR compounds with traditional antifungal agents, the therapeutically effective dose may be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information may be used to more accurately determine useful doses in humans. Levels in plasma may be measured, for example, by high performance liquid chromatography.

Results

Biological Evaluation

Inhibitory Activities of SR Compounds on *Candida* Hyphae Formation

Figure 3:
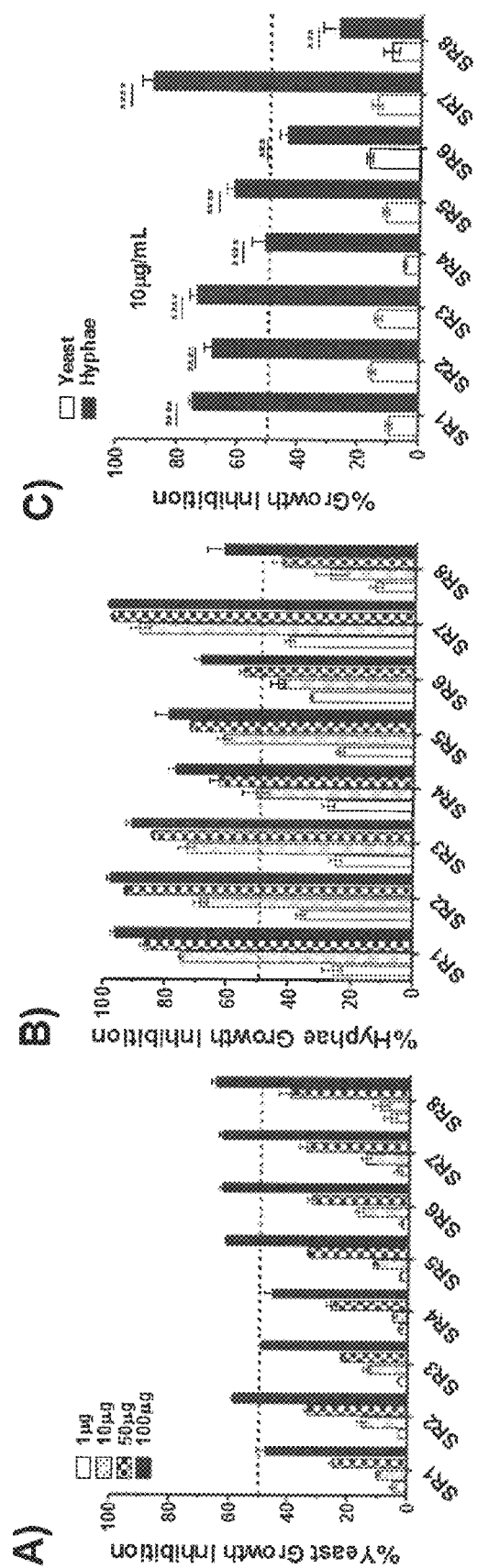
FIG. 3 reports anti-*C. albicans* activities of example SR compounds. (A) *Candida* yeast growth inhibition by SR compounds at different concentration (1, 10, 50, and 100 μg/mL). (B) Quantitative microtiter plate assay for biofilm formation using MTT assay method when *Candida* incubated with different concentration of the compounds (1, 10, 50, and 100 μg/mL) in *Candida* hyphae growth conditions (RPMI+2% Glucose at 37° C.). (C) Growth inhibition effects of SR compounds at 10 μg/mL on *Candida* when growing at either yeast or hyphae conditions. The effects of compounds were tested on *C. albicans* compared to solvent as negative control. The data was analyzed using two-way ANOVA and statistical significance was calculated with Bonferroni's multiple comparisons test and significance level indicated by asterisks (*, $P<0.05$; , $P<0.01$: *, $P<0.001$; ****, $P<0.0001$). The data display the mean±standard error (SEM) of three replicas.
Figure 4:
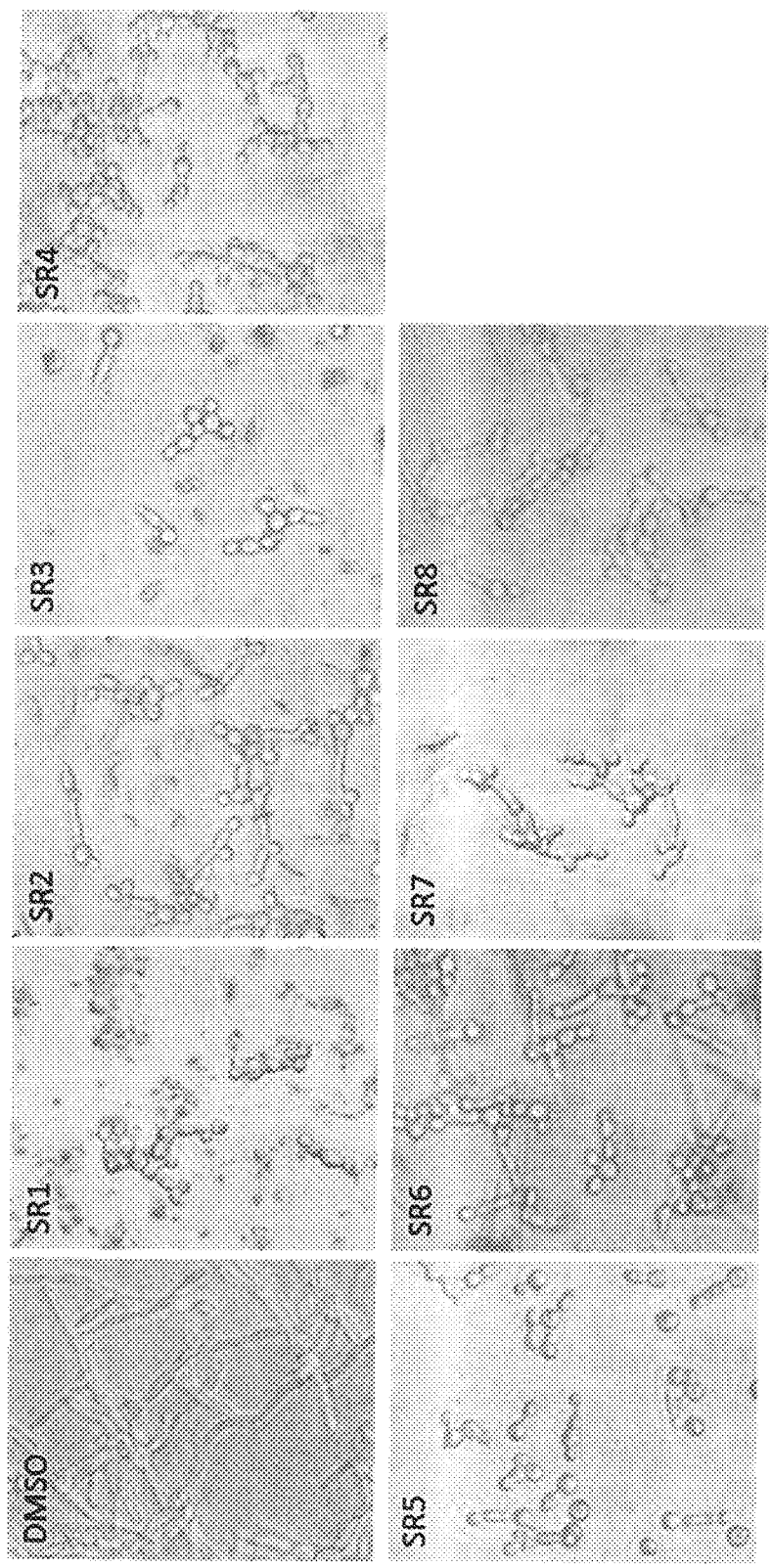
FIG. 4 illustrates the activity of SR compounds on hyphae formation of *C. albicans*. *Candida* at hyphae growth conditions were treated with 10 μg/mL of SR compounds and then incubated for 24 hrs at 37° C. The hyphae growth of *C. albicans* was followed by picturing using inverted microscopy. DMSO was employed as negative control.

The effect of newly-synthesized compounds, named SR1-8 (FIG. 2), on *C. albicans* growing either in yeast- or hyphae-forming conditions were tested separately at different concentrations including 1, 10, 50, 100 µg/mL. All tested concentrations showed weak inhibition activities against *C. albicans* yeast (FIG. 3A), while all compounds except compounds SR6 and SR8 showed significant inhibition activities (60-100%) against *Candida* hyphae in particular at concentrations 50 and 100 µg/mL (FIG. 3B). At the lower concentration of 10 µg/mL, all compounds showed inhibition of yeast at 10-20%, whereas compounds SR1-3 and 5 showed 60 to 80% hyphae inhibition. Furthermore, compounds SR4, 6 and 8 showed 50% hyphae inhibitory activities, while compound SR7 showed 90% inhibition activity (FIG. 3C). These results indicated that SR compounds were more effective against *C. albicans* hyphae formation compared to activity against yeast (two-way ANOVA, p<0.0001). Concordant with these results, the minimum inhibitory concentration of the compounds that resulted in 100% killing ($MIC_{100}$) against *C. albicans* yeast ranged from 125 µg/mL for compounds SR6, 7 and 8; 200 µg/mL for compounds SR2, 4 and 5; to 400 µg/mL for compounds SR1 and 3 (Table 1). In contrast, the $MIC_{100}$ that resulted in almost complete inhibition of biofilm formation (i.e. hyphal formation) ranged between 10-20 µg/mL (FIG. 4 and Table 1). Finally, the $MIC_{100}$ of the tested compounds ranged from 125-400 µg/mL against *E. coli* and >400 µg/mL against *Staphylococcus aureus* (Table 1). Collectively, these results confirmed that the newly designed compounds (SR) are *C. albicans* hyphae-specific inhibitors.

TABLE 1

Minimum inhibitory concentration (MIC) values in µg/mL of SR compounds against *C. albicans* and bacteria in 24 hrs incubation period. MIC is the lowest concentration of the compound that inhibited 100 of microbial growth.

| | MIC (µg/ml) | | | |
|---|---|---|---|---|
| | *C. albicans* | | Bacteria | |
| Compounds | Yeast | Hyphae | *E. Coli* | *S. aureus* |
| SR1 | >400 ± 15 | 20 ± 5 | 100 ± 10 | >400 |
| SR2 | 200 ± 15 | 10 ± 2 | 100 ± 10 | |
| SR3 | >400 ± 10 | 20 ± 5 | 400 ± 10 | |
| SR4 | 200 ± 10 | 20 ± 5 | 100 ± 10 | |
| SR5 | 200 ± 15 | 20 ± 3 | 400 ± 20 | |
| SR6 | 125 ± 10 | 10 ± 5 | 400 ± 10 | |
| SR7 | 125 ± 10 | 10 ± 3 | 100 ± 5 | |
| SR8 | 125 ± 10 | 20 ± 5 | 100 ± 10 | |
| Ketoconazole | 3 | NA | NA | NA |
| Colistin | NA | NA | 5 | NA |
| Vancomycin | NA | NA | NA | 3 |

Hyphal Inhibitory Activity of SR Compounds is Mediated Via TUP1 Activation

Figure 5:
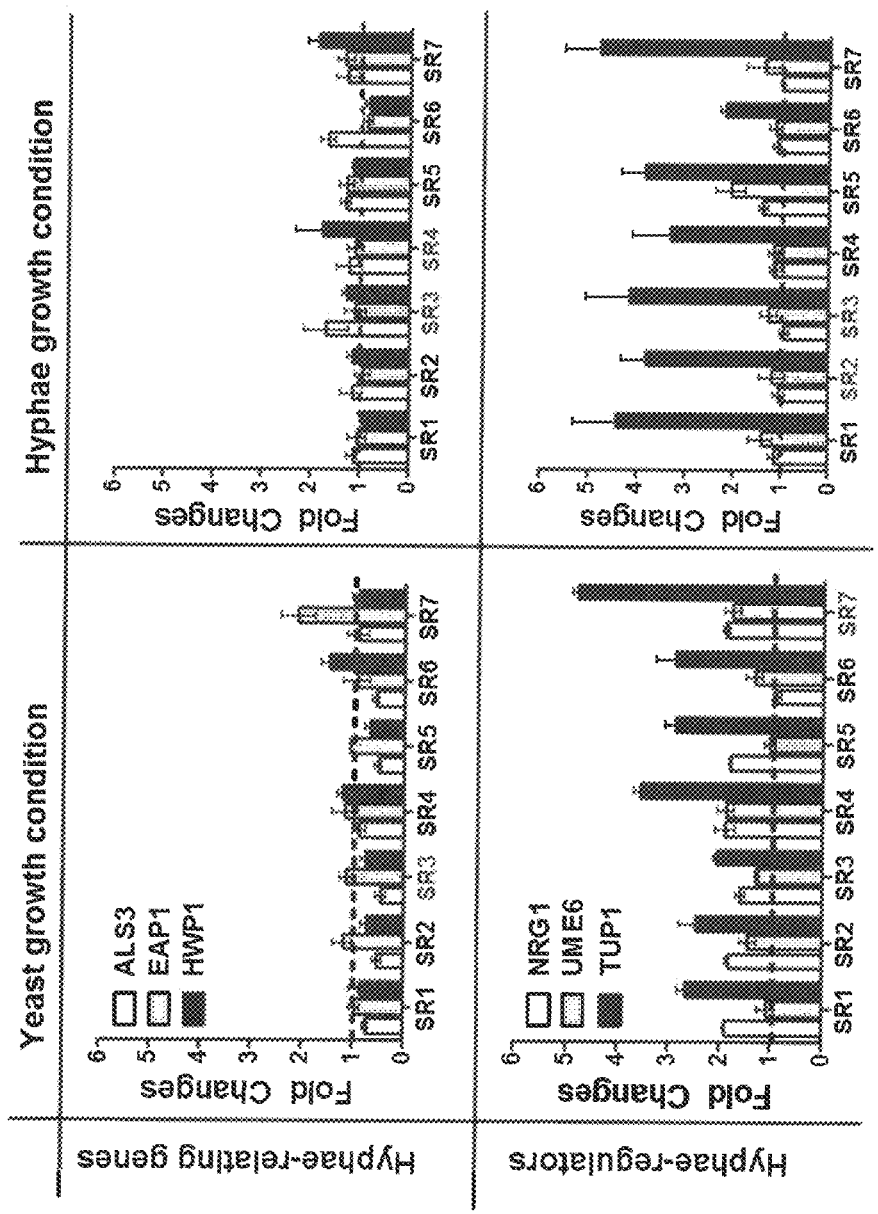
FIG. 5 illustrates gene expression analysis of *Candida* hyphae specific genes. *Candida* at either yeast or hyphae growth conditions were incubated with 10 μg/mL of SR compounds for 24 h. Quantitative real time PCR were performed using mRNA isolated from each condition. AL3; agglutinin-like sequence, EAP1; extracellular adhesion protein, HWP; hyphae cell wall protein, TUP1 and NRG1 are transcriptional repressor of filamentation and UME6 is transcriptional activator of filamentation. All data represented relative to fold changes compared to 18S rRNA housekeeping gene. Each figure has e transfers dotted line (equal 1) that represent the expression level of 18S rRNA housekeeping gene. The standard error represents the mean of three replicates.
Figure 6:
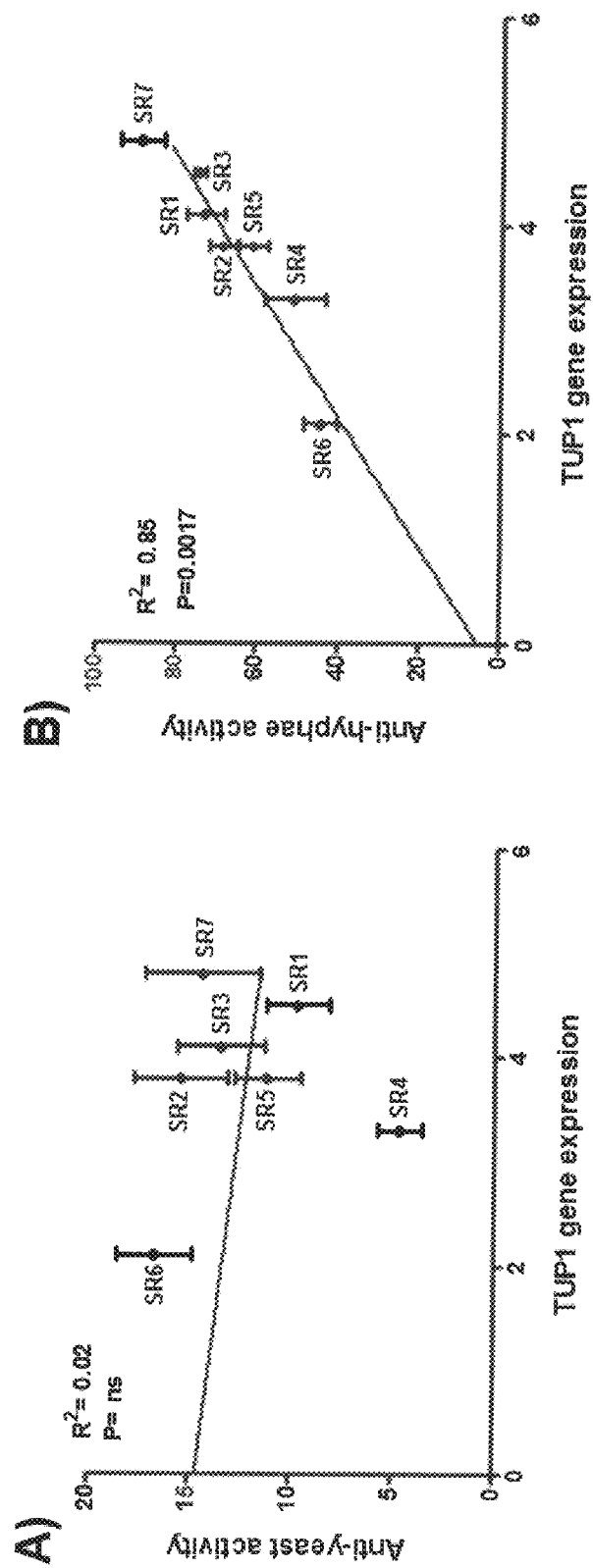
FIG. 6 illustrates the correlation between TUP1 gene expression and the anti-*C. albicans* activity. *Candida* at either yeast (A) or hyphae (B) growth conditions were incubated overnight with 10 μg/mL of SR compounds. In parallel, quantitative microtiter plate assay of the *Candida* activity at the end of experiment were measured by MTT viability assay. Gene expression data represented fold change compared to negative control while anti-*Candida* activities represented % growth inhibition compared to DMSO solvent as negative control. The data was analyzed using Pearson correlation and data considered normal distribution. P value<0.05 was considered significant.

To define the mechanism by which the SR inhibitors exerted their effect on *C. albicans* hyphae, we studied the effects of 7 synthesized compounds (SR 1-7) on the expression of genes that are known to either control *C. albicans* yeast/hyphal formation or are expressed in hyphae. The analysed genes included those associated with: (1) adhesion/invasion/biofilm formation such as HWP1 (hyphae cell wall protein), ALS3 (agglutinin-like sequence), EAP1 (extracellular adhesion protein); (2) the transcription activator UME6 responsible for hyphal formation; and (3) the transcription repressors of *Candida* filamentation (TUP1 and NRG1). At the yeast growth condition, all compounds showed significant increase in the expression level of TUP1 gene (FIG. 5). Compounds SR4, 5, 6, and 7 caused 3-4 fold increase in the expression of TUP1 gene compared to the expression level of 18S rRNA. Furthermore, all compounds except SR6 caused 2-fold increase in the expression of NRG1. In contrast, all other tested genes were not significantly changed. At the hyphae growth condition, all tested compounds caused ~4-5-fold increase in the expression level of TUP1 gene, while other genes were significantly not affected compared to the expression level of 18S rRNA gene (FIG. 5). Moreover, a study of the correlation between TUP1 gene expression levels and *C. albicans* inhibition activities by SR compounds either at yeast or hyphae growing conditions was conducted (FIG. 6). TUP1 gene expression showed strong direct correlation with hyphae inhibition activities ($r^2=0.85$) but not with yeast inhibition activity ($r^2=0.02$) (FIG. 6). The results from these studies indicated that SR compounds primarily exert their inhibitory effect on *C. albicans* hyphal formation through activation of the TUP1 hyphae repressor expression. Further, these studies revealed that SR7 is probably the best candidate for further development of prevention of *C. albicans* hyphal growth and biofilm formation.

3D QSAR Modelling Predicted the Enhanced Activity of Compound SR7

Figure 10:
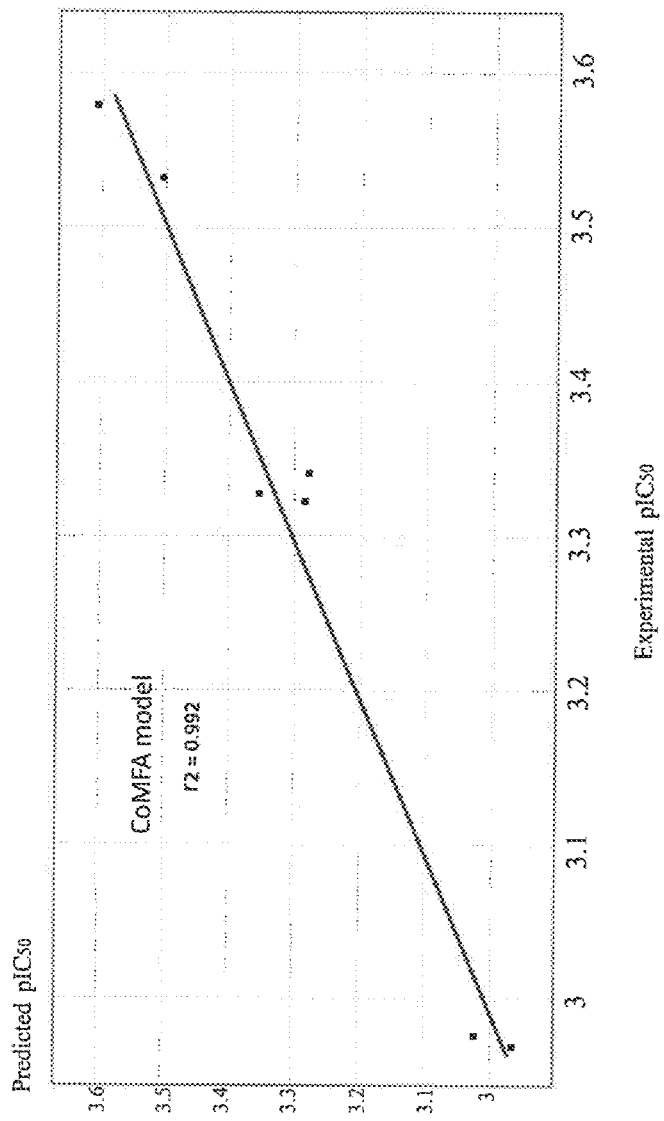
FIG. 10 is a graph of predicted $pIC_{50}$ versus experimental $pIC_{50}$ values of the training set obtained by PLS analysis using CoMFA models.

The relation of SR compounds structure to their concentration required for 50% inhibition [pIC50 (−log $IC_{50}$)] against *C. albicans* was also calculated using Comparative Molecular Field Analysis (CoMFA) steric and electrostatic interactions of each molecule, Partial Least square (PLS) and Leave-one-out (LOO) analyses. The results showed that the squared correlation coefficient ($r^2$) was 0.992 and the cross-validated correlation coefficient ($q^2$) was 0.50, while the standard deviation error of calculation (SDEC) was 0.021 and the standard deviation error of prediction (SDEP) was 0.165 (Table 2). The experimental activities, predicted activities, and their residuals are listed in Table 3. The correlation between the experimental activities and the predictive activities was 0.02 (FIG. 10). This correlation suggests the reliability and effectiveness of the established 3D QSAR model and its effectiveness in designing novel *C. albicans* inhibitors.

TABLE 2

Summary of CoMFA results

| PLS statistics | CoMFA |
|---|---|
| $r^2$ | 0.99 |
| $q^2$ | 0.50 |
| SDEC | 0.02 |
| SDEP | 0.16 |

TABLE 3

Experimental and predicted activities ($pIC_{50}$) of the training set molecules.

| No | $pIC_{50}$ Experimental | $pIC_{50}$ Predicted | Residual |
|---|---|---|---|
| SR1 | 2.968 | 2.967 | 0.001 |
| SR2 | 3.323 | 3.284 | 0.039 |
| SR3 | 2.975 | 3.025 | −0.050 |
| SR4 | 3.341 | 3.279 | 0.062 |
| SR5 | 3.328 | 3.353 | −0.025 |
| SR6 | 3.579 | 3.606 | −0.026 |
| SR7 | 3.579 | 3.605 | −0.026 |
| SR8 | 3.532 | 3.505 | 0.027 |

CoMFA steric contour maps are represented in FIG. 7A. The steric interactions are illustrated by green and yellow contours, while electrostatic interactions are denoted by red and blue contours (FIG. 7B). A large green contour (region A) and small green contour (region B) were found near the plane of the 3-$CF_3$ substituent of phenyl ring ($R_1$) and $OCH_3$ group in $R_2$ positions (compound SR7), respectively (FIG. 7A). This result suggested that bulky substituents were preferred in these two regions and indicated that they were important for the activity, thus explaining the highest activity of compound SR7. In contrast, a yellow contour (region C) was located around the 4-$CH_3$ substituent of phenyl ring ($R_1$) of compound SR1, indicating that groups with low steric factor were favored in this region to increase the activity and therefore explaining the decreased activity of compound SR1 (FIG. 7A). Blue-colored (region A) and red-colored (region B) contours represented the regions where the positively- and negatively-charged groups enhanced the activity, respectively (FIG. 7B). These results indicated that the electron-deficient substituents at 3-position of phenyl ring ($R_1$) were conducive to anti-hyphal activity, and electron-rich $R_1$ groups were preferred in the 4-position of the phenyl ring. In conclusion, CoMFA study revealed that positively-charged bulky groups were favored at position number 3 of the phenyl ring ($R_1$) and less steric, negatively-charged groups were favored at position number 4 of the phenyl ring ($R_1$). Furthermore, bulky group in position $R_2$ appeared to be conducive to anti-hyphal activity.

SR Compounds have Limited Toxicity and Efficient Metabolism

Figure 8:
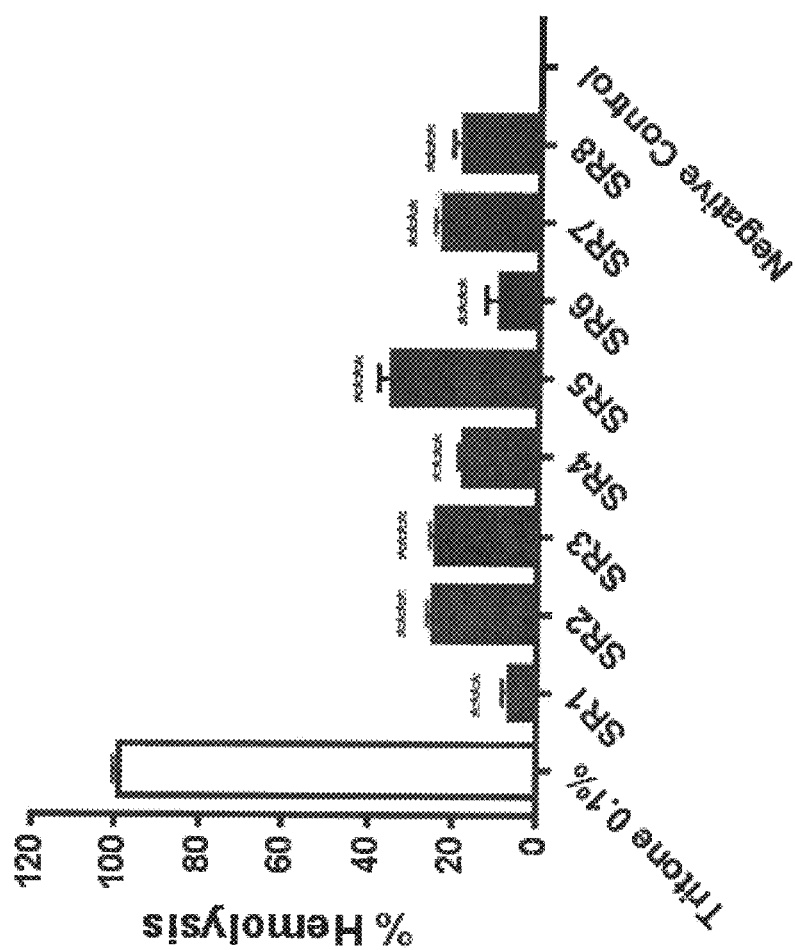
FIG. 8 illustrates the hemolytic activity of example SR compounds. DPBS-washed erythrocytes ($3 \times 10^6$ cells per well) were incubated in 96-well plate with 200 µg/mL of SR compounds at 37° C. for 30 min. The hemoglobin released from lysed erythrocytes was measured using micro-plate reader at 405 nm. The absorbance value for each sample was subtracted from the absorbance value of cells treated only with washing buffer and the hemolytic activity (%) was calculated. The data display the mean±standard error (SEM) of three independent measurements. The experiment was conducted in triplicate. ****P<0.0001 vs. 0.1% triton.

The cytotoxic activities of the compounds were examined by testing their hemolytic activities using human erythrocytes. Interestingly all compounds were significantly less toxic when compared to hemolysis caused by 0.1% triton (one-way ANOVA, p=0.0001). Specifically, at >200 µg/mL, a concentration that is 20× the $MIC_{100}$ required to inhibit hyphal formation, only 10-40% erythrocyte hemolysis was detected versus 100% hemolysis caused by 0.1% triton (FIG. 8). Furthermore, the physicochemical properties of the synthesized SR compounds were examined using theoretical prediction of absorption, distribution, metabolism, excretion, toxicity (ADMET) qualitative models via admet SAR server (https://www.lmmd.ecust.edu.cn/admetsar1/predict/) [18]. For instance, human intestinal absorption (HIA), cytochrome binding, biodegradation, acute oral toxicity, carcinogenicity, rat acute toxicity and aqueous solubility were calculated (FIG. 11). The calculations indicated that all compounds showed good intestinal absorption, good water solubility, and no inhibition of cytochromes. Hence, good metabolism and no toxicity of these compounds are predicted (FIG. 11). To investigate the absorption of the drug, total polar surface area (TPSA) of rhodanine derivatives were calculated. The TPSA of the compounds understudy was less than 140 Å which indicates the compounds are likely to be orally bio-available [19].

Discussion

Based on the inhibition activities of several synthesized thiazolidinedione [20], aromatic compounds such as 1,2-benzisothiazolinone [17] and rhodanine [14] derivatives on the *C. albicans* biofilm formation, several new hybrid compounds (SR1-8) featuring a rhodanine nucleus and aromatic side chain were developed in this study and their inhibitory potential on *C. albicans* hyphae formation were examined.

Figure 9:
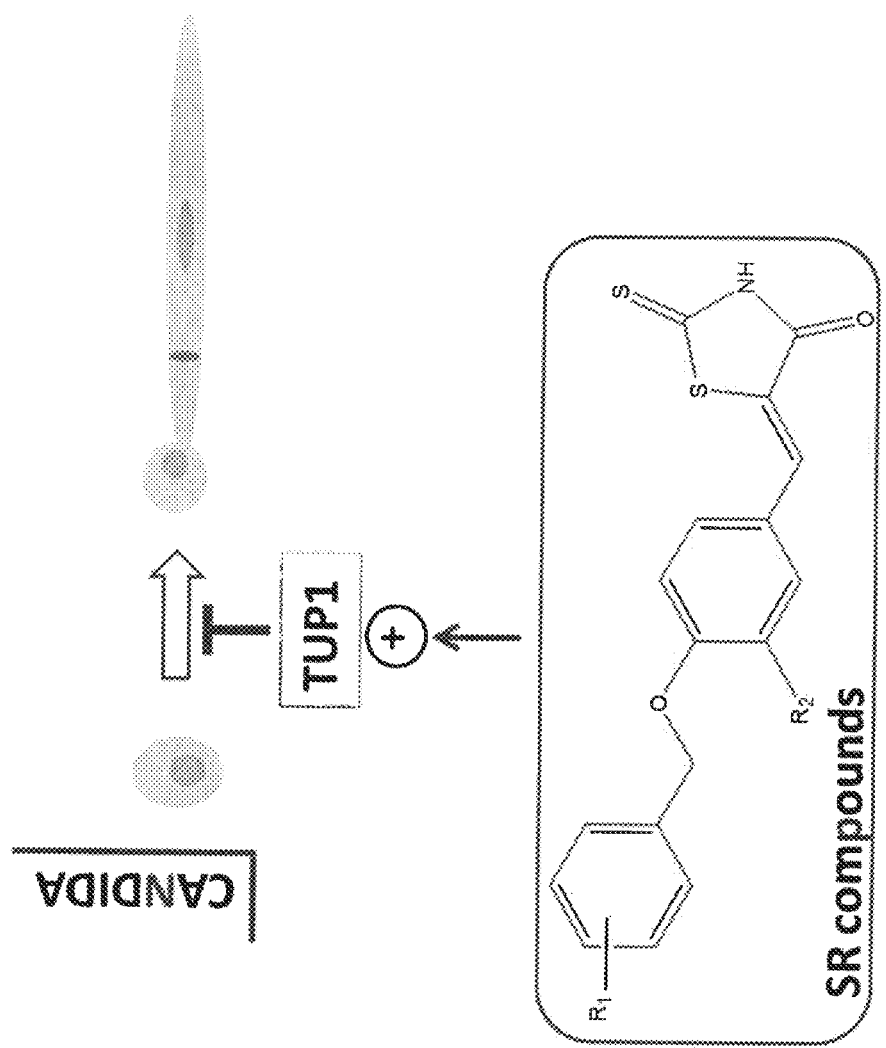
FIG. 9 is a model representing the inhibition effect of SR compounds on *C. albicans* hyphae growth. SR compounds caused significant up-regulation of TUP1 gene, which in turn inhibits hyphal growth in *C. albicans*.

The results showed that the newly-synthesized compounds (SR1-8) are inhibitors of *C. albicans* hyphae formation by activation of the hyphal repressor factor, TUP1. TUP1 is a critical transcription repressor that inhibits *Candida* hyphal formation by repressing the expression of hyphae-specific genes including CPH1 and UME6. Thus, up-regulation of TUP1 by SR compounds significantly contributed to the inhibition of *C. albicans* hyphal formation. However, we did not detect any significant changes in the expression of genes involved in *C. albicans* yeast/hyphal switch, adhesion or those expressed during hyphae growth including HWP1, ALS3, EAP1, and UME6, that is in accordance to previously reported data by Braun et al., 2000. Although the thiazolidinedione derivatives showed variable expression activities on *C. albicans* hyphae-associated genes, the newly-designed rhodanine derivatives were more selectively affecting TUP1 expression. Without being bound to any particular theory, the results indicate that SR compounds activated the expression of TUP1 repressor which in turn inhibited *Candida* hyphal formation without affecting *C. albicans* hyphae effector genes (FIG. 9).

The transcriptional repressor, TUP1 and the signalling molecule farnesol are both capable of negatively regulating the yeast-to-hyphae conversion. Specifically, it has been shown that TUP1 is up-regulated in *C. albicans* biofilms exposed to farnesol. Based on this overlap in function, we hypothesized that SR compounds are farnesol-like functioning despite the fact that they have completely different structures. Our data are consistent with the critical role of TUP1 in response to farnesol in *C. albicans*. Furthermore, it has been shown that the SR compounds required 10- to 40-fold increases over concentrations inhibiting hyphal formation to inhibit either *Candida* yeast or bacteria including *E. coli* or *S. aureus*. This finding is in accordance with the selective inhibitory effect of farnesol on *C. albicans* hyphal formation but not the yeast form. Both results confirmed the selective inhibitory effect of SR compounds on *C. albicans* hyphal formation.

TUP1 is known to function with the DNA binding proteins NRG1 to repress the expression of hypha-specific genes. However, our data indicated that SR compounds caused no significant increase in the expression of NRG1, indicating that the major effect of these inhibitors are on TUP1 rather than NRG1. In contrast, UME6, a key filament-specific transcription activator, known to be down regulated by TUP1 was not affected by SR compounds, indicative of a more likely signaling mechanism of hyphae activities by TUP1.

During infection, it is reported that *C. albicans* morphologies have distinct interactions with the host cells and activation of TUP1 results in significant reduction in *C. albicans* virulence, since yeast forms can be easily cleared from tissues by host defenses much more efficiently than hyphae. Our study indicated that the specificity and minimal toxicity of newly-designed compounds can be of special value particularly against *C. albicans* resistance forms (e.g. biofilm structures). Furthermore, the use of the new rhodanine derivatives in combination with available anti-fungal drugs may be considered as promising strategy to enhance treatment outcome of *C. albicans* infection.

Experimental Section

Chemistry

Most chemicals and solvents were of analytical grade and, when necessary, were purified and dried by standard methods. Reactions were monitored by thin-layer chromatography (TLC) using pre-coated silica gel plates (kiesel gel 60 F254, BDH), and spots were visualized under UV light (254 nm). Melting points were determined using a Gallenkamp melting point apparatus and are uncorrected. Column chromatography was performed with Merck silica gel 60 (40-60 µM). $^1$HNMR and $^{13}$CNMR spectra were recorded on a Bruker spectrometer at 500 MHz. Chemical shifts were expressed in parts per million (ppm) relative to tetramethylsilane, and coupling constant (J) values were represented in hertz (Hz) and the signals are designated as follows: s, singlet; d, doublet; t, triplet; m, multiplet. Mass spectroscopic data were obtained through Electrospray ionization (ESI) mass spectrum.

General Procedure for the Synthesis of 3-Substituted-4-(4-Substituedbenzyloxy) Benzaldehyde (R1-8):

To a mixture of substituted benzyl chloride (a-c) (10 mmol), $K_2CO_3$ (12 mmol) and KI (trace amount) in 20 mL acetonitrile, 3-substituted-4-hydroxybenzaldehde (d-f) was added drop wise under inert nitrogen and stirred overnight, then evaporated under reduced pressure. The crude mixture was quenched with water and the resulting undissolved solid was collected by filtration, washed with water, dried and recrystallized from aqueous ethanol to give the titled compound.

(1) 3-Methoxy-4-(4-methyl-benzyloxy)-benzaldehyde (R1), Yield: 75%, $^1$HNMR (DMSO-$d_6$. δ): 2.31 (s, 3H, $CH_3$), 3.83 (s, 3H, $OCH_3$), 5.17 (s, 2H, $CH_2$), 7.21 (d, 2H, j=8, ArH), 7.27 (d, 1H, j=8, ArH), 7.34 (d, 2H, j=8, ArH), 7.41 (d, 1H, j=2, ArH), 7.55 (dd, 1H, j=8, ArH), 9.84 (s, 1H, CHO).

(2) 3-Bromo-4-(4-methyl-benzyloxy)-benzaldehyde (R2), Yield: 79%, $^1$HNMR (DMSO-$d_6$. δ): 2.32 (s, 3H, $CH_3$), 5.30 (s, 2H, $CH_2$), 7.22 (d, 2H, j=8, ArH), 7.39 (m, 3H, ArH), 7.93 (d, 1H, j=8.5, ArH), 8.12 (d, 1H, j=2, ArH), 9.85 (s, 1H, CHO).

(3) 3-Chloro-4-(4-methyl-benzyloxy)-benzaldehyde (R3), Yield: 67%, $^1$HNMR (DMSO-$d_6$. δ): 2.31 (s, 3H, $CH_3$), 5.30 (s, 2H, $CH_2$), 7.22 (d, 2H, j=8, ArH), 7.36 (d, 2H, j=8, ArH), 7.44 (d, 1H, j=8.5, ArH), 7.87 (dd, 1H, j=8.5, ArH), 7.96 (d, 1H, j=2, ArH), 9.86 (s, 1H, CHO).

(4) 3-Methoxy-4-(4-trifluoromethyl-benzyloxy)-benzaldehyde (R4), Yield: 69%, $^1$HNMR (DMSO-d6. δ): 3.86 (s, 3H, $OCH_3$), 5.35 (s, 2H, $CH_2$), 7.25 (d, 1H, j=8, ArH), 7.44 (d, 1H, j=2, ArH), 7.56 (dd, 1H, j=8.5, ArH), 7.68 (d, 2H, j=8.5, ArH), 7.79 (d, 2H, j=8, ArH), 9.85 (s, 1H, CHO).

(5) 3-Bromo-4-(4-trifluoromethyl-benzyloxy)-benzaldehyde (R5), Yield: 72%, 1HNMR (DMSO-$d_6$. δ): 5.48 (s, 2H, $CH_2$), 7.41 (d, 1H, j=8, ArH), 7.72 (d, 2H, j=8.5, ArH), 7.81 (d, 2H, j=8, ArH), 7.95 (dd, 1H, j=8.5, ArH), 8.15 (d, 1H, j=2, ArH), 9.87 (s, 1H, CHO).

(6) 3-Bromo-4-(3-trifluoromethyl-benzyloxy)-benzaldehyde (R6), Yield: 74%, $^1$HNMR (DMSO-$d_6$. δ): 5.46 (s, 2H, $CH_2$), 7.42 (d, 1H, j=8.5, ArH), 7.73 (m, 2H, ArH), 7.81 (d, 1H, j=7.5, ArH), 7.89 (s, 1H, ArH), 7.95 (dd, 1H, j=8.5, ArH), 8.15 (d, 1H, j=2, ArH), 9.84 (s, 1H, CHO).

(7) 3-Methoxy-4-(3-trifluoromethyl-benzyloxy)-benzaldehyde (R7), Yield: 79%, $^1$HNMR (DMSO-$d_6$. δ): 3.86 (s, 3H, $OCH_3$), 5.34 (s, 2H, $CH_2$), 7.28 (d, 1H, j=8.5, ArH), 7.44 (d, 1H, j=2, ArH), 7.57 (dd, 1H, j=8.5, ArH), 7.67 (m, 1H, ArH), 7.73 (d, 1H, j=7.5, ArH), 7.75 (d, 1H, j=7.5, ArH), 7.85 (s, 1H, ArH), 9.86 (s, 1H, CHO).

(8) 3-Chloro-4-(4-trifluoromethyl-benzyloxy)-benzaldehyde (R8), Yield: 69%, $^1$HNMR (DMSO-$d_6$. δ): 5.46 (s, 2H, $CH_2$), 7.49 (d, 1H, j=8.5, ArH), 7.70 (m, 1H, ArH), 7.76 (d, 1H, j=8.0, ArH), 7.82 (d, 1H, j=7.5, ArH), 7.88 (s, 1H, ArH), 7.93 (dd, 1H, j=8.5, ArH), 8.0 (d, 1H, j=2, ArH), 9.88 (s, 1H, CHO).

General Procedure for the Synthesis of 5-[3-Substitued-4-(4-Substituedbenzyloxy)-Benzylidene]-2-Thioxo-Thiazolidin-4-One (SR1-8)

A mixture of the appropriate aldehyde R(1-8) (10 mmol), rhodanine (20 mmol) and β-alanine (20 mmole) in glacial acetic acid (10 mL) was heated at 100° C. in an oil bath for 3 h. After cooling to room temperature, the reaction was poured into crushed ice and the precipitate was filtered, washed with water and dried. The crude product was purified by recrystallization from DMF/EtOH.

5-[3-Methoxy-4-(4-methyl-benzyloxy)-benzylidene]-2-thioxo-thiazolidin-4-one (SR1), Yield: 77%, MP 205-207. $^1$HNMR (DMSO-$d_6$. δ): 2.31 (s, 3H, $CH_3$), 3.03 (s, 3H, $OCH_3$), 5.13 (s, 2H, $CH_2$), 7.19 (m, 5H, ArH), 7.35 (d, 2H, j=8, ArH), 7.56 (s, 1H, ArH), 13.75 (s, 1H, NH), $^{13}$C NMR (DMSO-d6. δ): 20.83, 55.64, 69.89, 113.62, 122.51, 124.49, 125.87, 128.09, 132.23, 133.42, 137.41, 149.33, 150.28, 169.50, 195.53. MS analysis for $C_{19}H_{17}NO_3S_2$ Calculated mass 371.06, found (m/z, ESI+) ($M^+$+1): 372.10.

(2) 5-[3-Bromo-4-(4-methyl-benzyloxy)-benzylidene]-2-thioxo-thiazolidin-4-one (SR2), Yield: 85%, MP 217-219. $^1$HNMR (DMSO-d6. δ): 2.31 (s, 3H, $CH_3$), 5.26 (s, 2H, $CH_2$), 7.23 (d, 2H, j=8, ArH), 7.39 (d, 3H, j=6.5, ArH), 7.56 (dd, 1H, j=2, ArH), 7.60 (s, 1H, ArH), 9.89 (d, 1H, j=2, ArH), 13.82 (s, 1H, NH). $^{13}$ CNMR (DMSO-$d_6$. δ): 20.80, 30.71, 70.39, 112.13, 114.68, 124.12, 127.17, 127.66, 129.13, 130.20, 131.04, 133.0, 135.44, 137.46, 156.24, 206.56. MS analysis for $C_{18}H_{14}BrNO_2S_2$ Calculated mass 418.96, found (m/z, ESI+) ($M^+$+1): 421.88

(3) 5-[3-Chloro-4-(4-methyl-benzyloxy)-benzylidene]-2-thioxo-thiazolidin-4-one (SR3), Yield: 82%, MP 225-227. $^1$HNMR (DMSO-d6. δ): 2.31 (s, 3H, $CH_3$), 5.24 (s, 2H, $CH_2$), 7.22 (d, 2H, j=7.5, ArH), 7.38 (m, 3H, ArH), 7.51 (dd, 1H, j=8.5, ArH), 7.57 (s, 1H, ArH), 7.71 (d, 1H, j=2, ArH), 13.91 (s, 1H, NH). $^{13}$ C NMR (DMSO-$d_6$. δ): 20.81, 30.34, 114.87, 122.51, 124.32, 126.69, 127.78, 129.14, 130.15, 130.43, 132.34, 132.96, 137.53, 155.32, 169.64, 195.43. MS analysis for $C_{18}H_{14}ClNO_2S_2$ Calculated mass 375.02, found (m/z, ESI+) ($M^+$+1): 376.01.

(4) 5-[3-Methoxy-4-(4-trifluoromethyl-benzyloxy)-benzylidene]-2-thioxo-thiazolidin-4-one (SR4), Yield 66%, MP 209-211. $^1$HNMR (DMSO-$d_6$. δ): 3.86 (s, 3H, $OCH_3$), 5.32 (s, 2H, $CH_2$), 7.23 (m, 3H, ArH), 7.61 (s, 1H, ArH), 7.68 (d, 2H, j=8, ArH), 7.79 (d, 2H, j=8, ArH), 13.77 (s, 1H, NH). $^{13}$ CNMR (DMSO-$d_6$. δ): MS analysis for $C_{19}H_{14}F_3NO_3S_2$ Calculated mass 425.4 found (m/z, ESI+) ($M^+$+1): 426.17.

(5) 5-[3-Bromo-4-(4-trifluoromethyl-benzyloxy)-benzylidene]-2-thioxo-thiazolidin-4-one (SR5), Yield: 68%, MP 210-212. $^1$H-NMR (DMSO-$d_6$. δ): 5.43 (s, 2H, $CH_2$), 7.37 (d, 1H, j=8.5, ArH), 7.58 (dd, 1H, j=9, ArH), 7.60 (s, 1H, ArH), 7.71 (d, 2H, j=8.5, ArH), 7.81 (d, 2H, j=8, ArH), 7.91 (d, 1H, j=2, ArH), 13.83 (s, 1H, NH). $^{13}$CNMR (DMSO-$d_6$. δ): 30.72, 69.52, 112.09, 114.63, 124.32, 125.29, 127.50, 130.18, 131.08, 135.52, 140.97, 155.89, 169.36, 195.30, 206.59. MS analysis for $C_{18}H_{11}BrF_3NO_2S_2$ Calculated mass 472.94, found (m/z, ESI+) ($M^+$+1): 475.94.

(6) 5-[3-Bromo-4-(3-trifluoromethyl-benzyloxy)-benzylidene]-2-thioxo-thiazolidin-4-one (SR6), Yield: 65%, MP 235-237. $^1$HNMR (DMSO-d$_6$. δ): 5.42 (s, 2H, CH$_2$), 7.4 (d, 1H, j=8, ArH), 7.61 (m, 2H, ArH), 7.63 (m, 1H, ArH), 7.66 (d, 1H, j=7.5, ArH), 7.70 (d, 1H, j=7.5, ArH), 7.74 (s, 1H, ArH)), 7.80 (d, 1H, j=7.5, ArH), 13.83 (s, 1H, NH). $^{13}$CNMR (DMSO-d$_6$. δ): 69.55, 112.13, 114.66, 123.83, 124.81, 125.27, 127.52, 128.92, 129.42, 130.14, 131.12, 133.46, 135.53, 137.67, 155.94, 169.39, 172.10, 195.33. MS analysis for C$_{18}$H$_{11}$BrF$_3$NO$_2$S$_2$ Calculated mass: 472.94, found (m/z, ESI+) (M$^+$+1): 475.94.

(7) 5-[3-Methoxy-4-(3-trifluoromethyl-benzyloxy)-benzylidene]-2-thioxo-thiazolidin-4-one (SR7), Yield: 67%, MP 199-201. $^1$HNMR (DMSO-d$_6$. δ): 3.85 (s, 3H, OCH$_3$), 5.30 (s, 2H, CH$_2$), 7.23 (m, 3H, ArH), 7.62 (s, 1H, ArH), 7.66 (m, 1H, ArH), 7.73 (d, 1H, j=7.5, ArH), 7.78 (d, 1H, j=7.5, ArH), 7.85 (s, 1H, ArH), 13.77 (s, 1H, NH). $^{13}$CNMR (DMSO-d$_6$. δ): 55.70, 69.12, 113.83, 122.78, 124.35, 124.77, 124.80, 126.27, 129.67, 131.88, 132.12, 138.05, 149.36, 149.88, 162.332, 169.41, 195.51. MS analysis for C$_{19}$H$_{14}$F$_3$NO$_3$S$_2$ Calculated mass 425.4, found (m/z, ESI+) (M$^+$+1): 426.17

(8) 5-[3-Chloro-4-(3-trifluoromethyl-benzyloxy)-benzylidene]-2-thioxo-thiazolidin-4-one (SR8), Yield 74%, MP 224-226. $^1$H-NMR (DMSO-d6. δ): 5.46 (s, 2H, CH$_2$), 7.44 (d, 1H, j=8.5, ArH), 7.54 (dd, 1H, j=9, ArH), 7.60 (s, 1H, ArH), 7.68 (m, 1H, ArH), 7.73 (m, 2H, ArH), 7.75 (d, 1H, j=7, ArH), 7.76 (s, 1H, ArH), 13.83 (s, 1H, NH). $^{13}$C NMR (DMSO-d6. δ): 69.50, 114.89, 122.53, 123.96, 124.02, 124.93, 125.27, 127.16, 128.93, 129.18, 129.43, 129.80, 130.46, 131.58, 132.38, 137.64, 154.97, 195.72. MS analysis for C$_{18}$H$_{11}$ClF$_3$NO$_2$S$_2$ Calculated mass: 428.99, found (m/z, ESI+) (M$^+$+1): 429.88.

Biological Evaluation

Organisms and Growth Conditions

Collections of bacterial and fungal strains were obtained from the laboratory of Dr. Ibrahim at Harbor-UCLA medical center, Torrance, Calif. The bacterial strains used in this study were the Gram-negative bacterium *Escherichia coli* and the Gram-Positive bacterium methicillin-resistant *Staphylococcus aureus* (MRSA) LAC300. All bacterial strains were cultured on sterile Luria-Bertani medium (LB). The fungal strain used in this study was *C. albicans* SC5314. *C. albicans* was inoculated into sterile yeast potato dextrose broth (YPD) and incubated for 24 h at 37° C. (This was used as an initial culture for all studies described), and incubated in two different media, Yeast Nitrogen Base (YNB) broth or Roswell Park Memorial Institute medium (RPMI-1640). Polymyxin B (colistin), vancomycin and Ketoconazole were purchased from (Sigma-Aldrich).

Determination of Antimicrobial Activity

The antimicrobial activity of compounds SR1-8 on agar plates, liquid broth media and MIC were measured according to modified Clinical and Laboratory Standards Institute (CLSI). Briefly, 0.1 mL containing 10$^5$ CFU/mL was spread on Luria-Bertani (LB) agar plates. The plates were then incubated at 37° C. for 34 h with filter discs (8 mm diameter) saturated with different dilutions of the compounds (1-400 μg/mL). The inhibition zones (mm) were measured by determining the diameter of the clear area. Similarly, the activity in liquid media was measured by incubating the aforementioned concentrations of the compounds into LB broth media inoculated with 10$^5$ CFU/mL in 96-well microplates at 37° C. for 24 h. The turbidity representing the microbial growth was measured by microplate reader (DYNEX technologies) at OD$_{600}$. The MIC was the lowest concentration of the compound that prevented microbial growth (showed no turbidity). Each test was performed in triplicate. Ketoconazole, colistin and vancomycin were employed as positive controls against *C. albicans, E. coli* and *S. aureus* bacteria, respectively. Cultures without the compounds or antimicrobials were employed as negative control.

Inhibition of *Candida* Biofilm Formation

The MICs for cells forming biofilm were determined by a microtiter plate assay. Briefly, a 96-well polystyrene microtiter plate was seeded with 200 μL of RPMI-1640 containing 10$^6$ *C. albicans* cells in the presence of the compound of interest at concentration range of 1-100 μg/mL. After 24 h of incubation at 37° C., the biofilms were washed and the fungal viability was analyzed using 3-(4,5-dimethylthiazol-2-yl)-2,5-diphenyl tetrazolium bromide (MTT) (Sigma) and the final absorbance was measured at 540 nm. The assay was performed in triplicate and repeated three times. The MIC of the compounds causing 100% inhibition of *C. albicans* biofilm formation was determined by measuring the metabolic activity of biofilm compared to solvent control.

Quantitative Real Time RT-PCR Analysis of *C. albicans* Hyphae/Biofilm Formation Specific Genes To quantify the expression of *C. albicans* hyphae-specific genes (Table 4), *Candida* cells were grown in either yeast (YNB) or hyphae/biofilm (RPMI 1640 media) growing conditions as described previously in the presence of compounds SR1-8 at 10 μg/mL. The cultures were incubated in 6-well plates for 24 h at 37° C. For yeast growing conditions, the cultures were collected separately, centrifuged and the pellets were washed by PBS prior to RNA extraction, cDNA synthesis and gene expression analysis. For hyphae growing conditions, the cultures were centrifuged, and the isolated hyphae were washed with PBS. RNA extraction was performed using Ribopure™ RNA purification kit (ThermoFisher) following the manufacturer's manual. Contaminating genomic DNA was removed from RNA samples by treatment with 4 μL of Turbo-DNaseI (Invitrogen) for 30 min at room temperature. DNase was then removed using DNase inactivation reagent (Invitrogen). First-strand cDNA synthesis was performed using the Retroscript first-strand synthesis kit (Ambion). The amplification efficiency was determined by serial dilution experiments, and the resulting efficiency coefficient was used for the quantification of the products. Gene expression was analyzed by an ABI Prism 7000 Sequence Detection System (Applied Biosystems) using the Power SYBR green PCR master mix (Applied Biosystems). PCR conditions were 10 min at 90° C. and 40 cycles of 15 s at 95° C. and 1 min at 60° C. Single PCR products were confirmed with the heat dissociation protocol at the end of the PCR cycles. The amount of gene expression was normalized to 18S rRNA and then quantified using the 2(−ΔΔC(T)) method. All reactions were performed in triplicate, and the mixture included a negative no-reverse transcription (RT) control in which reverse transcriptase was omitted.

TABLE 4

Oligonucleotides used in the present study

| Primer name | Primer sequence (5'-3') | Ref |
|---|---|---|
| ALS3 | Forward; CAACTTGGGTTATTGAAACAAAAACA<br>Reverse; AGAAACAGAAACCCAAGAACAACC | [40] |
| EAP1 | Forward; TGTGATGGCGGTTCTTGTTC<br>Reverse; GGTAGTGACGGTGATGATAGTGACA | [41] |

TABLE 4-continued

Oligonucleotides used in the present study

| Primer name | Primer sequence (5'-3') | Ref |
|---|---|---|
| NRG1 | Forward; CCAAGTACCTCCACCAGCAT<br>Reverse; GGGAGTTGGCCAGTAAATCA | [42] |
| TUP1 | Forward; CTTGGAGTTGGCCCATAGAA<br>Reverse; TGGTGCCACAATCTGTTGTT | [42] |
| HWP1 | Forward; GCTCCTGCTCCTGAAATGAC<br>Reverse; CTGGAGCAATTGGTGAGGTT | [42] |
| UME6 | Forward; ACCACCACTACCACCACCAC<br>Reverse; TATCCCCATTTCCAAGTCCA | [43] |
| 18S rRNA | Forward; CACGACGGAGTTTCACAAGA<br>Reverse; CGATGGAAGTTTGAGGCAAT | [34] |

Correlation Between Anti-*C. albicans* Activities of the Compounds and TUP1 Gene Expression In order to determine how strong the relationship was between TUP1 gene expression and either the anti-yeast or anti-hyphal activities of the synthesized SR compounds, a formula was generated using Graph Pad 5.0 to produce what is referred to as the coefficient value. A Pearson's correlation attempts to draw a line of best fit through the data of two variables (TUP1 gene expression and anti-*C. albicans* activities of the compounds), where each row represented a different compound, the X column represented the TUP1 gene expression and the Y columns represented the anti-*C. albicans* activities of the compound against either yeast or hyphae forms. The Pearson correlation coefficient, r, indicates how far away all these data points are to this line of best fit. A value of −1 is representing a perfect negative linear relationship, while +1 for a perfect positive linear relationship.

Quantitative Structure-Activity Relationship (QSAR) Studies

To explore the correlation between the 3D structures of the training set (SR1-8) and their biological activities, a predictive 3D QSAR model was built. Comparative Molecular Field Analysis (CoMFA) was used to build the 3D QSAR model using Py-CoMFA 3D QSAR service. CoMFA calculates steric and electrostatic properties of each molecule on 3D cubic lattice with grids pacing of 2° A in x, y, and z directions using the Tripos force field. An sp³ carbon atom probe with a Vander Waals radius of 1.52° A and a charge of þ 1.0 was used to generate the steric and electrostatic (Coulombic potential) field with a distance-dependent dielectric at each lattice point. The steric and electrostatic energy values were truncated at 30.0 Kcal/mol. The minimum sigma (column filtering) was set to 0.05 Kcal/mol. Equal weights for CoMFA were assigned to steric and electrostatic fields using CoMFA STD scaling option. The regression analysis was carried out using the partial least squares (PLS) analysis and the cross validation was carried with leave-one-out (LOO) method in which one compound is removed from the data set and its activity is predicted using the model derived from the rest of the molecules in the dataset.

Cytotoxicity Assay

The cytotoxic assay of SR compounds was measured by quantifying the amount of hemoglobin released by lysis of human erythrocytes as previously described. Briefly, fresh whole blood from healthy individual was collected by venipuncture and the blood was immediately centrifuged at 500 g for 10 min using benchtop centrifuge (Eppendorf 5804R Refrigerated Benchtop). The erythrocytes were washed and re-suspended to $3 \times 10^7$ cells/mL in DPBS followed by incubation with the compounds in round-bottomed 96-well plates in a final volume of 200 μL. Washing buffer and 0.1% Triton X-100 were used as negative and positive controls, respectively. The plate was incubated at 37° C. for 30 min, and the intact cells were precipitated by centrifugation at 500 g for 10 min at 4° C. and the supernatants (125 μL) were transferred to a flat-bottom 96-well plate to measure hemoglobin release by absorbance at 405 nm using a microplate reader. The absorbance values for each sample were subtracted from the absorbance value obtained for washing buffer-treated cells and the hemolytic activity (%) was calculated. The experiment was conducted in triplicate.

Blood samples were collected after obtaining a signed informed consent from healthy volunteers under an approved Los Angeles Biomedical Research Institute IRB protocol #11671.

Statistical Analysis

The data was graphed using Graph Pad 5.0 for Windows (GraphPad Software, La Jolla, Calif., USA). The statistical significance was analyzed using one-way or two-way analysis of variance (ANOVA) using either Bonferroni's multiple comparisons test or Dunn's Multiple Comparison Test. P value<0.05 was considered significant.

Definitions

As used in this description and the accompanying claims, the following terms shall have the meanings indicated, unless the context otherwise requires:

As used herein, "treatment" is understood to refer to the administration of a drug or drugs to a patient suffering *Candida albicans* infection.

As used herein, the term "therapeutically effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

What is claimed is:

1. A compound of Formula (SR):

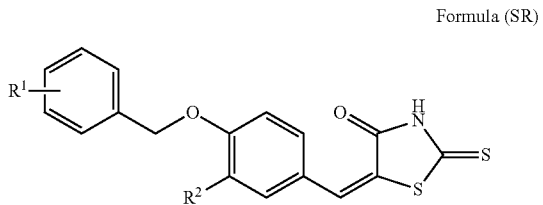

Formula (SR)

wherein:
R$^1$ is selected from R$^3$, SR$^3$, N(R$^3$)$_2$, , C(O)OR$^3$, NR$^3$C(O)R$^3$, C(O)NR$^3$, SO$_2$R$^3$, NR$^3$SO$_2$R$^3$, and SO$_2$N(R$^3$)$_2$;
R$^3$ is a C$_1$-C$_5$ alkyl group optionally substituted with one or more halogen atoms;
R$^2$ is a halogen atom, CN, NO$_2$, OR$^4$, SR$^4$, N(R$^4$)$_2$, C(O)R$^4$, C(O)OR$^4$, NR$^4$C(O)R$^4$, C(O)NR$^4$, SO$_2$R$^4$, NR$^4$SO$_2$R$^4$, and SO$_2$N(R$^4$)$_2$;
R$^4$ is a C$_1$-C$_5$ alkyl group optionally substituted with one or more halogen atoms.

2. A compound according to claim 1, wherein R$^3$ is selected from CH$_3$, CH$_2$X, CHX$_2$, and CX$_3$, wherein X is a halogen atom.

3. A compound according to claim 1, wherein R$^3$ is selected from CH$_3$ and CF$_3$.

4. A compound according to claim 1, wherein R$^4$ is selected from CH$_3$, CH$_2$X, CHX$_2$, and CX$_3$, wherein X is a halogen atom.

5. A compound according to claim 1, wherein R$^1$ is CF$_3$ and R$^2$ is OCH$_3$.

6. A compound according to claim 1, the compound being of Formula (SR1) or Formula (SR2):

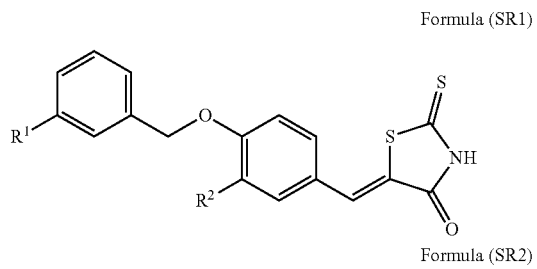

Formula (SR1)

Formula (SR2)

7. A therapeutic composition for treating, suppressing, or reducing the severity of hyphal formation, the composition comprising a compound according to claim 1.

8. A method of treating, suppressing, or reducing the severity of hyphal formation in a subject with a fungal infection, the method comprising administering to the subject a therapeutic amount of a compound of Formula (SR):

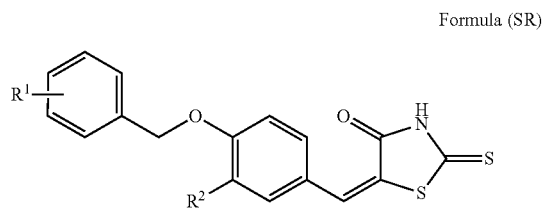

Formula (SR)

wherein:
R$^1$ is selected from a halogen atom, CN, NO$_2$, R$^3$, OR$^3$, SR$^3$, N(R$^3$)$_2$, C(O)R$^3$, C(O)OR$^3$, NR$^3$C(O)R$^3$, C(O)NR$^3$, SO$_2$R$^3$, NR$^3$SO$_2$R$^3$, and SO$_2$N(R$^3$)$_2$;
R$^3$ is a C$_1$-C$_5$ alkyl group optionally substituted with one or more halogen atoms;
R$^2$ is a halogen atom, CN, NO$_2$, R$^4$, OR$^4$, SR$^4$, N(R$^4$)$_2$, C(O)R$^4$, C(O)OR$^4$, NR$^4$C(O)R$^4$, C(O)NR$^4$, SO$_2$R$^4$, NR$^4$SO$_2$R$^4$, and SO$_2$N(R$^4$)$_2$;
R$^4$ is a C$_1$-C$_5$ alkyl group optionally substituted with one or more halogen atoms.

9. A method according to claim 8, wherein R$^3$ is selected from CH$_3$, CH$_2$X, CHX$_2$, and CX$_3$, wherein X is a halogen atom.

10. A method according to claim 8, wherein R$^3$ is selected from CH$_3$ and CF$_3$.

11. A method according to claim 8, wherein R$^4$ is selected from CH$_3$, CH$_2$X, CHX$_2$, and CX$_3$, wherein X is a halogen atom.

12. A method according to claim 8, wherein R$^1$ is CF$_3$ and R$^2$ is OCH$_3$.

13. A method according to claim 8, wherein the compound is of Formula (SR1) or Formula (SR2):

Formula (SR1)

-continued

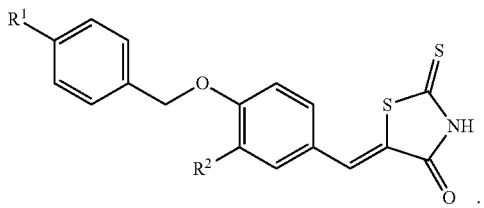

Formula (SR2)

14. A method according to claim 8, wherein the fungal infection is a yeast of the genus *Candida*.

15. A method according to claim 8, wherein the fungal infection is *Candida albicans*.

16. A therapeutic combination of drugs for the treatment of a fungal infection, the combination comprising a compound according to claim 1 and an antifungal agent.

17. The therapeutic combination of drugs of claim 16, wherein the antifungal agent is selected from the group consisting of azole antifungals, echinocandins, polyenes, griseofulvin, terbinafine, flucytosine, terbinafine, and combinations thereof.

18. In a method of treating, suppressing, or reducing the severity of a fungal infection in a subject, the method comprising: administering a first amount of an antifungal agent, the improvement comprising administering to the subject a second amount of a compound according to claim 1.

19. A method according to claim 18, wherein the fungal infection is of the genus *Candida*.

20. A method according to claim 18, wherein the fungal infection is *Candida albicans*.

* * * * *